(12) United States Patent
Liu

(10) Patent No.: US 8,444,920 B2
(45) Date of Patent: May 21, 2013

(54) O-RING SYSTEMS AND METHODS FOR QUANTIFICATION OF MULTIPLEX BIOMARKERS IN MULTIPLE SAMPLES

(76) Inventor: Weiqun Liu, San Francisco, CA (US)

( * ) Notice: Subject to any disclaimer, the term of this patent is extended or adjusted under 35 U.S.C. 154(b) by 669 days.

(21) Appl. No.: 12/561,123

(22) Filed: Sep. 16, 2009

(65) Prior Publication Data

US 2011/0065133 A1 Mar. 17, 2011

(51) Int. Cl.
 *C12Q 1/68* (2006.01)
(52) U.S. Cl.
 USPC ............................................................ 422/50
(58) Field of Classification Search
 None
 See application file for complete search history.

(56) References Cited

U.S. PATENT DOCUMENTS 7,693,369 B2 * 4/2010 Fan et al. ........................ 385/32
2002/0197739 A1 * 12/2002 Prinz et al. .................... 436/518

* cited by examiner

*Primary Examiner* — Ann Lam
(74) *Attorney, Agent, or Firm* — Baumgartner Patent Law; Marc Baumgartner

(57) ABSTRACT

Kits and methods of using O-rings having apertures are provided herein. O-rings are useful for incubating with a sample fluid potentially having one or more biomarkers, in order to detect the presence of the biomarkers. O-rings can be readily organized in a trackable manner prior to and during incubation with the sample fluid. O-rings can also be readily transferred and organized into one or more trackable arrays for detecting the presence of bound biomarkers and measuring the signaling product generated by bound detect molecule-linked enzymes present in a homogeneous solution with a spectrophotometer.

11 Claims, 9 Drawing Sheets

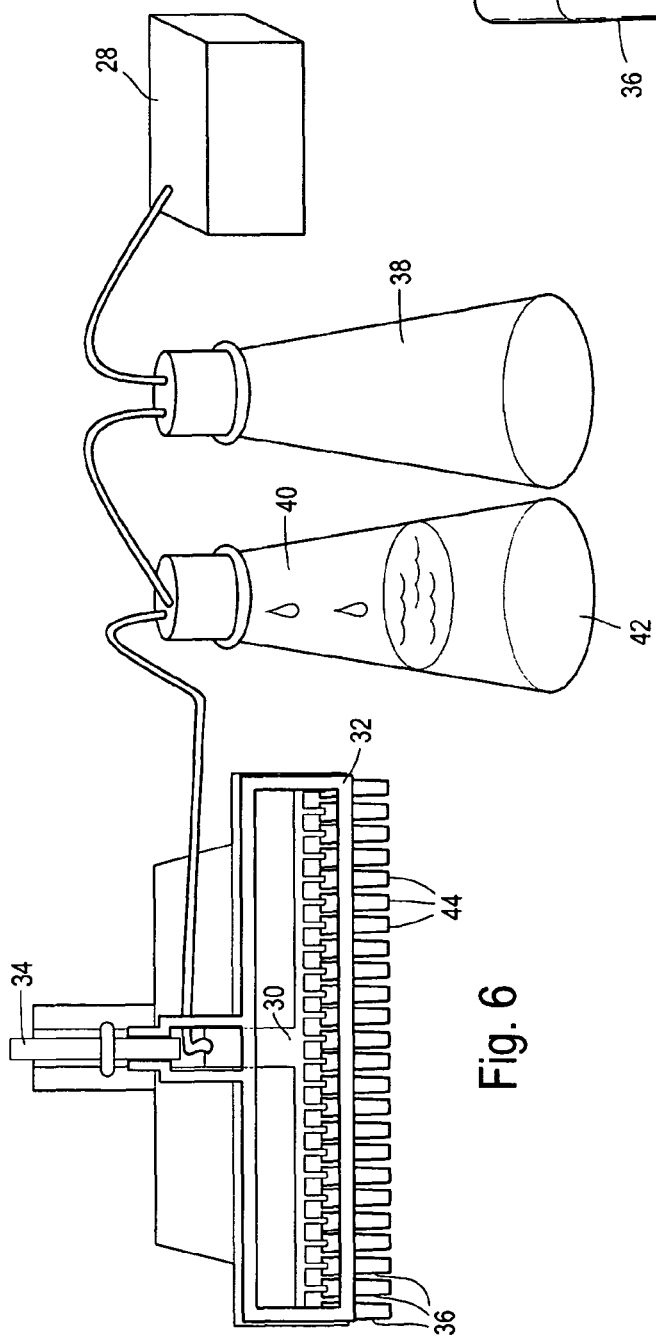
Fig. 6
Fig. 7

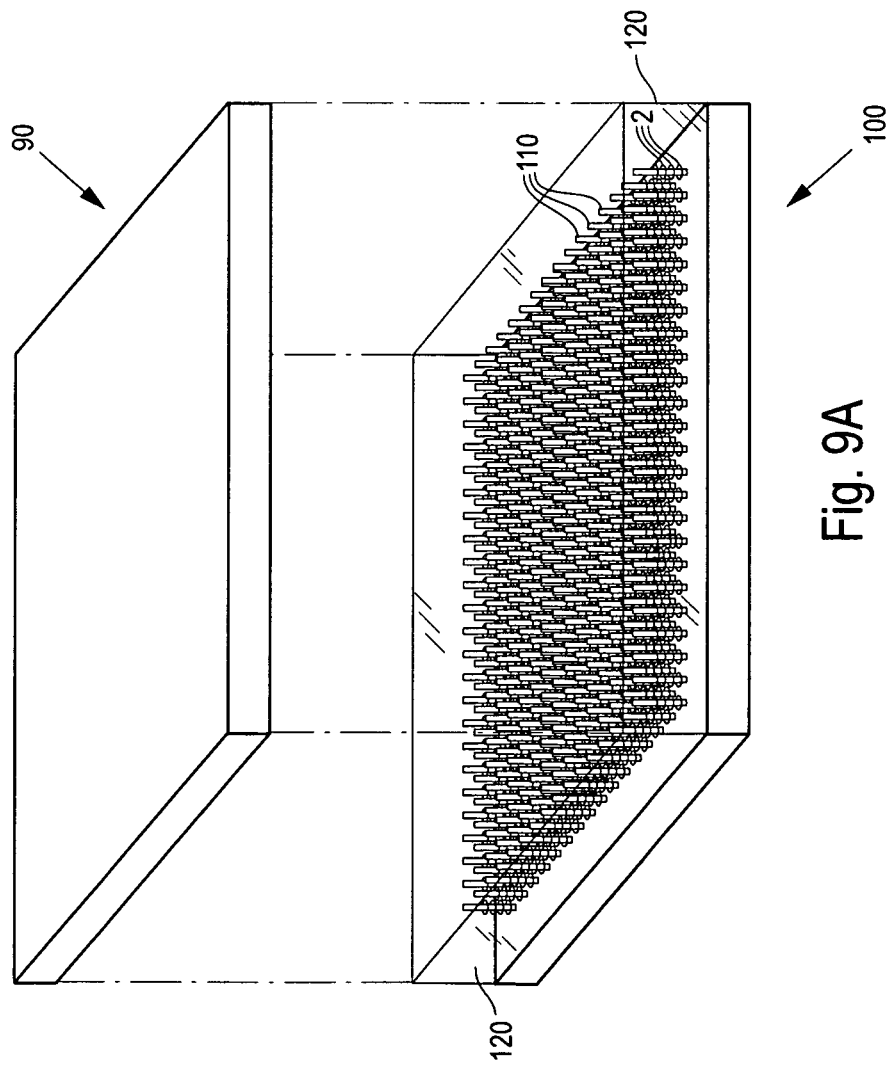
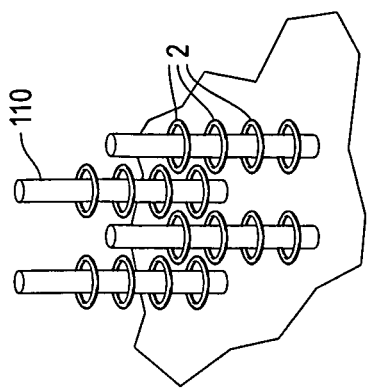

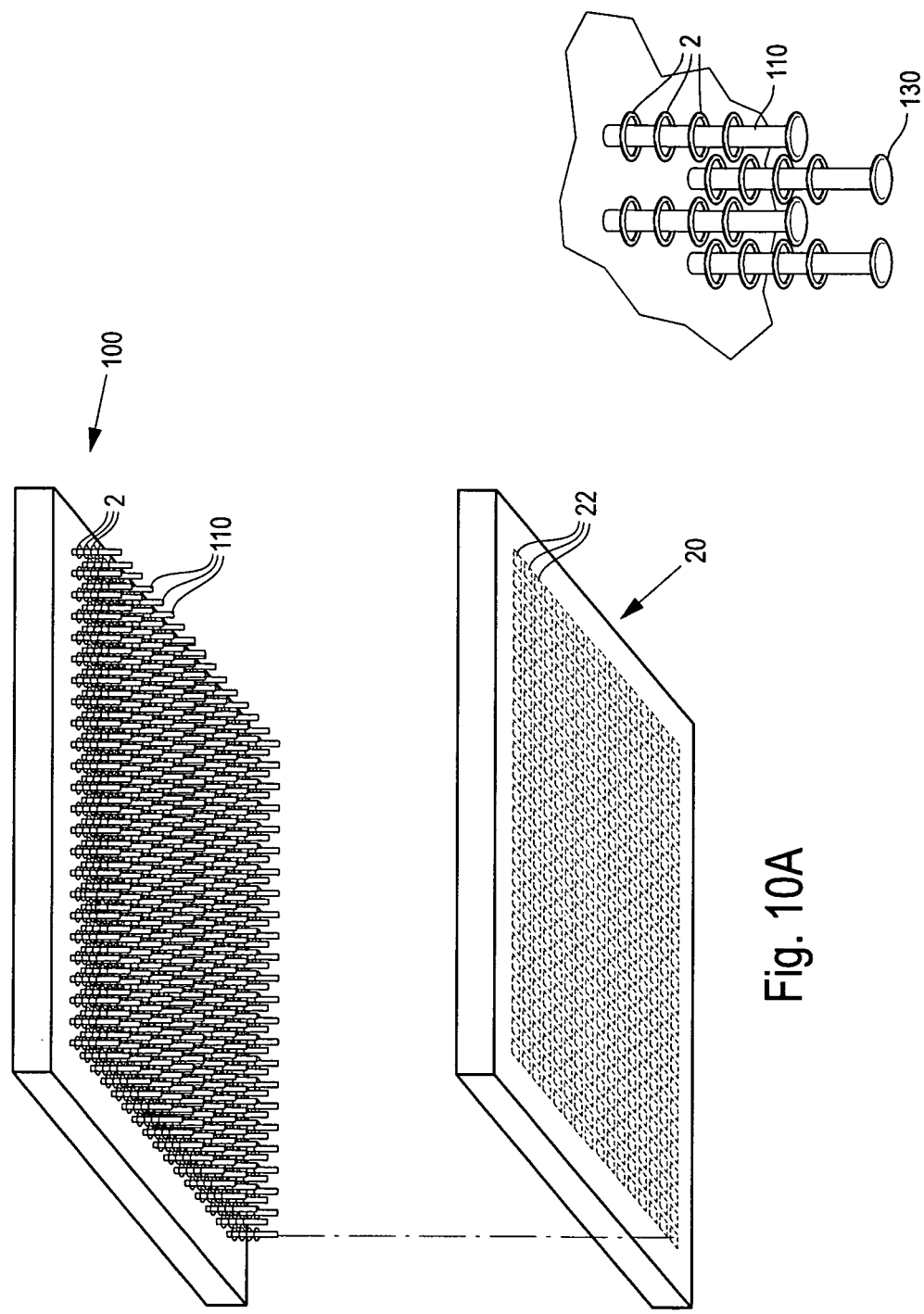

O-RING SYSTEMS AND METHODS FOR QUANTIFICATION OF MULTIPLEX BIOMARKERS IN MULTIPLE SAMPLES

FIELD OF THE INVENTION

The teachings herein relate to new O-ring systems and methods of using the same for detecting and quantifying multiplex biomarkers in a sample.

BACKGROUND

The proteome can be defined as the entire complement of proteins, including the post-translation-modified proteins, produced within an organism, tissue type, or a cell. Proteomics is a study of such entire protein complements, particularly their qualitative and quantitative changes in structure and expression resulting from the stimuli, stress and function of a living organism.

In order to address such structural and expressional changes in a partial or entire complement of proteins within a cell, numerous methods for high-multiplex biomarker quantification have emerged from several major categories of technologies: 2-dimensional electrophoresis, mass-spectrometry and immunoassays. Those technologies have already enabled the gathering of an unprecedented level of functional proteomic information as they have answered a large number of critical questions regarding multiple types of human diseases and environmental impact on human health. However, these methods face major challenges in meeting the clinical requirement for accuracy, reproducibility, sensitivity and specificity with respect to high throughput multiplex detection. Particularly, it remains very difficult for many of these methods to simultaneously detect and accurately quantify multiple samples of high-multiplex protein biomarkers that are run in parallel, simultaneously.

Many Double-Antibody-Sandwich Enzyme-Linked Immunosorbent Assays (DAS-ELISA) for a single biomarker have already been approved by the F.D.A. for clinic diagnostic measurement of multiple samples, due to the fact that these assays can pass the vigorous trials and tests for reliability, accuracy, sensitivity and specificity at multiple clinic and research centers. In the past decade, a huge effort has already been spent to incorporate the principles of the single-biomarker ELSIA into multiplex biomarker immunoassays for the testing of multiple samples using the analogue of microarray based genomic technology. Three major categories of ELISA microarrays currently exist: (1) planar slide arrays, (2) sphere bead arrays and, (3) micro-fluidic chip arrays. The multiplex detection with respect to micro-fluidic chips is in its infant stage and has very little data published as of yet.

In general, ELISA microarrays utilize some of the principles and antibody materials of traditional DAS-ELISA. For example, capture-antibodies are typically selected for having a first region that will couple to the surface of a solid substrate (e.g., planar slide or bead) and another region capable of binding to one of the targeted biomarkers that is potentially present in the sample. After first binding to the substrate, the capture-antibody is exposed to the sample and the biomarker (s) present therein. After allowing the biomarkers present in the sample to bind to the targeted regions of their respective capture-antibodies, a fluorescent or chemoluminescent-linked detect-antibody can be added to the substrate and allowed to bind to the exposed region (unbound region) of the biomarker to form a sandwich-like complex on the surface of the microarray support substrates. The intensity of the fluorescence or chemiluminescence signal from the complex can then be quantified, in order to estimate the concentration of the target biomarkers in the sample using an imaging device. This can be done by comparing the sample's signal to a known, or standard, signal.

Importantly however, previous multiplex-microarrays significantly deviate from the essential, original procedure of traditional single-biomarker DAS-ELISA. For example, the image-based signal quantification method is different from spectrometry used by traditional DAS-ELISA. Particularly, because the fluorescent or chemoluminescent signals on the surface of microarray substrate matrix are non-homogeneous, non-uniform and non-even, quantification by an imaging device is much less reproducible and sensitive than the counterpart from a homogeneous enzyme-substrate solution by spectrometer. Additionally, with respect to open microarrays (slides and beads), because multiple types of multiplex detect-antibodies are pre-mixed before they are allowed to probe the captured biomarker complexes, one of the detect antibodies may potentially form a non-specific sandwich complex with an unintended captured biomarker, thus indicating a false positive. This problem does not occur with traditional DAS-ELISA because the single captured-biomarker assay is only probed with one type of detect antibody. Furthermore, in planar slide microarrays, as each sample is processed on a microarray slide, each of the samples and their standard controls have to be processed separately on their own individual microarray slide. In practice, it is very difficult to simultaneously process the multiple samples and standard controls in parallel during the incubation and washing, probing and quantifying procedures, especially if the sample volume is in short supply. In beads based microarrays, the same biomarker is not simultaneously quantified among all of the samples and their standard controls in parallel. Thus, with respect to bead based arrays, the higher the number of multiplex biomarkers there are to be quantified, the wider the time gap will be for the quantification of the same biomarker.

Clearly, planar slides-based and sphere beads-based ELISA microarray technologies confine their users to carefully balance between their needs of biomarker multiplexing capacity (significance of proteomic bias), high throughput capacity (total number of standards and samples) and quantification reliability (related to accuracy, reproducibility, specificity and sensitivity). Other problems of those microarrays often happen after the printing of slide microarrays or the coupling of sphere beads with the capture-antibodies to the support surface. These problems can include the inactivation of antibodies due to storage instability, the changing of binding affinity between biomarker, capture antibodies, detect antibodies and support substrate surface due to inconsistent timing and handling.

To resolve the above-mentioned challenges, one of the general objectives herein is to maintain, or substantially maintain, the accuracy, reproducibility, specificity and sensitivity of biomarker quantification of traditional DAS-ELISAs during multiplex biomarker quantification of multiple small volume samples. The teachings herein encompass both new materials and methods related to a new multiplex microarray.

SUMMARY OF THE INVENTION

Embodiments herein are directed to methods of detecting the presence of one or more biomarkers in a fluid, comprising providing a fluid that potentially contains one or more biomarkers; providing one or more O-rings, each individually comprising an aperture; coating the one or more O-rings with a coupling reagent to enhance binding to one or more capture molecules; covalently coupling one or more capture molecules with the one or more O-rings, to form one or more O-ring/capture molecule complexes, wherein each capture molecule is selected to bind to the one or more biomarkers potentially present in the fluid; incubating the one or more O-ring/capture molecule complexes with the fluid to sufficiently allow binding between the one or more capture molecules and their respective biomarkers so as to form one or more O-ring/capture molecule/biomarker complexes; and detecting the presence of the one or more biomarkers in the one or more O-ring/capture molecule/biomarker complexes.

Further methods include a plurality O-rings of substantially the same size and shape are provided and arranged in a trackable order after covalently coupling with a plurality of capture molecules and prior to incubating with the fluid. The trackable order can be a column of stacked O-ring/capture molecule complexes, for example.

More specifically, a column of stacked O-ring/capture molecule complexes can be positioned inside a sealable container via a probe that traverses through the apertures of the O-rings, such that the positional order of the O-rings is maintained during incubation with the fluid. Alternatively the column of stacked O-ring/capture molecule complexes can be positioned on a pin in a pin plate, such that the pin traverses through the apertures of the O-rings and maintains the positional order of the O-rings during incubation with the fluid.

According to other embodiments, O-rings can be individually covalently coupled to a plurality of capture molecules such that no O-ring contains more than one particular type of capture molecule.

After incubation with the fluid, the plurality of O-ring/capture molecule/biomarker complexes can be transferred in a trackable order and formed into an array on a microplate, wherein only one O-ring/capture molecule/biomarker complex is placed in a single well on the microplate.

Further embodiments are directed to kits for incubating one or more O-rings with a sample fluid to allow binding to one or more biomarkers potentially present in the fluid, comprising: one or more O-rings, each individually comprising an aperture; a container configured to hold the one or more O-rings and the sample fluid such that the one or more O-rings can bind with the one or more biomarkers potentially present in the fluid via affinity chromatography.

More specifically, the kits can include a plurality of O-rings that are of substantially the same size and shape, and are capable of binding to a plurality of biomarkers potentially present in the sample fluid. Additionally, the O-rings can be coated with a coupling reagent to enhance binding to the plurality of biomarkers potentially present in the sample fluid.

The kits can further include a plurality of capture molecules capable of covalently coupling with the plurality of O-rings, to form a plurality of O-ring/capture molecule complexes, wherein each capture molecule is selected to bind to a particular type of biomarker potentially present in the fluid.

The container in the kits can be a pin plate having a plurality of pins configured to pass through the apertures of the plurality of O-rings. More specifically, the multiple pins can individually traverse through the apertures of multiple O-rings, such that said multiple O-rings are stacked in a trackable order on a given pin.

Alternatively, the kit's container can be a deep well microplate, wherein a plurality of deep wells are configured to hold the plurality of O-rings. More specifically, the multiple wells can individually hold multiple O-rings, such that said multiple O-rings are stacked in a trackable order in a given well.

Additional embodiments are directed to methods of detecting the presence of one or more biomarkers in a fluid, comprising: providing a fluid that potentially contains one or more biomarkers; providing one or more O-rings, each individually comprising an aperture; coating the one or more O-rings with a coupling reagent to enhance binding to one or more biomarkers, incubating the one or more O-rings with the fluid to sufficiently allow binding with the one or more biomarkers so as to form one or more O-ring/biomarker complexes; and detecting the presence of the one or more biomarkers in the one or more O-ring/biomarker complexes.

The method can include a plurality O-rings of substantially the same size and shape that are provided and arranged in a trackable order prior to incubating with the fluid to bind to a plurality of biomarkers. According to certain methods, prior to incubation, the plurality of O-rings can be coated with a coupling reagent to enhance binding to the plurality of biomarkers potentially present in the sample fluid. Additionally, the plurality of O-rings can be arranged in a trackable order on a pin plate having a plurality of pins configured to traverse through the apertures of the plurality of O-rings.

According to further embodiments, after incubation with the fluid, the plurality of O-ring/biomarker complexes can be transferred in a trackable order and formed into an array on a welled microplate, wherein only one O-ring/biomarker complex is placed in a single well on the microplate.

Further embodiments include methods of measuring the concentration of a signaling product comprising providing a plurality of biomarker complexes, that individually comprise an O-ring and a plurality of biomarkers; arranging said biomarker complexes individually into single wells on a microplate; providing a plurality of detect molecule-linked enzyme complexes that are selected to bind to the plurality of biomarkers and are capable of producing a measurable signaling product when contacted with a substrate specific for said linked enzyme in a reactive solution; adding said detect molecule-linked enzyme complexes to the wells on the microplate such that the detect molecules bind to the biomarkers in the biomarker complexes; adding said substrate in the reactive solution to the wells on the microplates such that it comes into contact with bound detect molecule-linked enzyme complexes; and measuring the signaling product produced by the bound detect molecule-linked enzyme complexes and the reactive solution.

BRIEF DESCRIPTION OF THE DRAWINGS

FIG. 6 depicts a multi-channel O-ring Pipette system for transferring and sorting O-rings
FIG. 7 depicts a disposable pipette tip
FIG. 9A depicts a walled pin plate and a reservoir lid, devoid of wells, wherein the pins are configured to traverse through the apertures of a plurality of O-rings.
FIG. 9B depicts a close up of a plurality of O-rings positioned on pins.

FIG. 10A. depicts a pin plate and a storage welled microplate, wherein the pins are configured to traverse through the apertures of a plurality of O-rings and to fit within each well of the microplate.

FIG. 10B depicts a close up of a plurality of O-rings positioned on pins with a retainer.

Figure 1B:
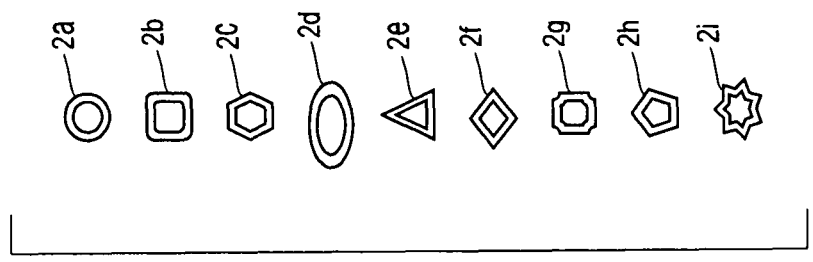
FIG. 1B depicts various alternative O-ring shapes.

It will be appreciated that the drawings are not necessarily to scale, with emphasis instead being placed on illustrating the various aspects and features of embodiments of the invention.

DETAILED DESCRIPTION OF THE ILLUSTRATED EMBODIMENTS

Embodiments of the present invention are described below. It is, however, expressly noted that the present invention is not limited to these embodiments, but rather the intention is that modifications that are apparent to the person skilled in the art and equivalents thereof are also included.

Terms

O-ring: The term "O-ring", can relate to various three-dimensional shapes, non-exclusively including rings or toroids. For example, an O-ring can be spherical, cubical, cuboidal, conical, cylindrical, pyramidal, prism shaped, or ellipsoid, for example. An opening, preferably in the center, is configured to allow a probe, pin, or other member to pass through. According to more specific embodiments, the O-ring is a symmetrical 3-D shape having a central axis running through the aperture. While dissimilar shaped and sized O-rings could be utilized herein, they are not-preferred. More specifically, the utilization herein of solid O-rings having uniform shape and size, or substantially so, greatly ensures that the substrate coated surface area of all O-rings is capable of coupling the same, sufficient amount of a capture molecule (e.g., capture antibody). According to further embodiments, the O-rings are in the shape of a ring, or toroid, and are configured to rest within a well, such as tightly in the bottom of the well, of a standard 96- or 384-well microplate. According to certain embodiments, the teachings herein relate to an array of O-rings covalently coupled with a one or more capture molecules such as biomarker-specific antibodies, or other high affinity molecules.

Synthetic Polymer: The term "polymer" refers to a large molecule (macromolecule) composed of repeating structural units typically connected by covalent chemical bonds. The term "synthetic" means man-made, or something new from two or more pre-existing elements, in contrast to the term "natural". The natural polymers have a large class of natural materials with a variety of properties, such as protein, nucleic acids, polysaccharides and lipids. According to certain teachings herein, synthetic polymers are used to make the O-rings, including but not limited to polymers, such as polystyrene, which contains other copolymers such as divinylbenzene; polymethylmethacrylate (PMMA); polyvinyltoluene (PVT); copolymers such as styrene/butadiene, styrene/vinyltoluene, and latex. Examples of polymers that can be used to make the O-rings can non-exclusively include large molecules (macromolecules) composed of repeating structural units typically connected by covalent chemical bonds, including Bakelite, neoprene, nylon, polyvinyl chloride (PVC), polystyrene, polyacrylonitrile, polyvinyl butyral (PVB), silicone, fluoropolymer or fluoroelastomer, for example.

Bind: The term "bind", as used herein, generally relates to a variety of interactions that are not covalent in nature between molecules or parts of molecules that provide force to hold the molecules or parts of molecules together, usually in a specific orientation or conformation. According to the teachings herein, the capture molecule is used to bind one unique part of a biomarker molecule and the detect molecule is used to bind another part of the same biomarker, thus allowing the formation of dual-molecule (e.g., antibody) sandwich complex. Often, the term "bind" can be exchanged with the term "probe", though the latter is meant with the proactive attempt and intention of subject whereas the former means the mutual interaction.

Couple: The term "couple", as used herein, relates to attachment by covalent bonds or by strong non-covalent interactions, typically and preferably to attachment by covalent bonds. Any method normally used by those skilled in the art for the coupling of biologically active materials can be used in the present invention.

Organosilicone coupling reagent: The term "organosilicone coupling reagent" refers to a group of compounds having two functional groups with different reactivity. One of the two functional groups reacts with organic materials and the other reacts with inorganic materials. Their general structure is as follows: Y—R—Si—(X)3, where Y denotes a functional group that links with organic materials, e.g. vinyl, epoxy, amino group and so on. X is a functional group that undergoes hydrolysis by water or moisture to form silanol that is capable of coupling to inorganic materials. Representative examples of X include chlorine, alkoxy, and acetoxy group. According to the teachings of herein, 3-glycidoxypropyl-trimethoxysilane (GOPS) is used to first couple to the polymer support substrate of O-rings with by silanol linkage and secondarily couple to the amino group of antibodies or other proteins with its functional group epoxy. Because the surface of polymer O-rings can be highly porous, the coupling reagents can tremendously increase the effective surface area of polymer O-rings at 3-dimensional directions and multi-layer levels.

Biomarker: The term "biomarker" as used herein broadly relates to biological molecules that may be present in a sample or standard fluid and that are targeted to be bound or recognized by the "capture molecule" and/or the "detect molecule" for further analysis, detection, or quantification. Biomarkers can include, but are not limited to, proteins, peptides, hormones, haptens, antigens, antibodies, receptors, enzymes, nucleic acids, polysaccharides, polymers, pathogens, toxins, organic drugs, inorganic drugs, dyes, cells, tissues, microorganisms, viruses, bacteria, fungi, algae, parasites, allergens, pollutants and combinations thereof. It will be understood that detection of, for example, a cell, is typically carried out by detecting a particular component, such as a cell-surface molecule, and that both the component and the bacteria as a whole can be described as the biomarker.

Sort: The term "sort" relates to separating O-rings coupled to the same targeted biomarker complex with the specific capture antibody or with the specific detect antibody from the other O-rings coupled to different biomarker complexes.

Rearrange: The terms "rearrange" and "transferring" generally relates to the concept and procedure that converts an array of sequential multi-layer O-rings positioned in a chromatograph column format, such as in a deep well in a storage microplate (96 well or 384 well microplate), or a cylindrical container, or a cylindrical tube, into one or more arrays of single O-rings per well in fresh ELISA microplates (96 well or 384 well microplate). This can non-exclusively be done after the column of O-rings have pre-coupled respectively to different capture molecules.

Antigen: The term "antigen" relates to a substance that stimulates antibody generation and/or causes an immune response and that can be recognized by the specific antibodies. The word "antigen" originated from the notion that the antibodies may be stimulated and recognized by their highly corresponding substances. Antigens are usually described as proteins or polysaccharides or their derivatives, including the parts (coats, capsules, cell walls, flagella, fimbrae, and toxins) of bacteria, viruses, and other microorganisms, or non-microbial exogenous protein or polysaccharide or their derivatives. Generally, lipids and nucleic acids can become antigens when conjugated with proteins and polysaccharides. According to the teachings herein, an antigen can be used to characterize the specific antibodies utilized in the ELISA arrays.

Antibody: The term "antibody" generally relates to a group of gamma globulin proteins (also known as immunoglobulins, abbreviated Ig) produced and released into blood or other bodily fluids by the immune system of vertebrates and used to recognize and neutralize the exogenous objects, such as bacteria and viruses. According to their biochemical properties, antibodies consist of basic units, each with two large heavy chains of peptide and two small light chains of peptide to form monomers with one unit in a "Y" shape-like structure, or dimers with two units or pentamers with five units. A small region of heavy and light chains within a monomer unit is extremely variable, allowing millions of antibodies to form a huge diversity of different antigen binding structures. According to the teachings herein, though antibodies are capable of other vital functions in vivo, such as the neutralization of a pathogenic antigen via direct binding activities or the initiation of other immunity reaction against an antigen, the highly specific recognizing and binding interaction of antibodies respectively with antigens and the huge diversity of specific antibodies against the equally huge diversity of antigens of research interest are utilized in this multiplex biomarker immunoassay in vitro. Noticeably, the diversity of vertebrate species for antibody production dramatically increases not only the opportunity and diversity of antigens to be identified and recognized, but also the complexity of technology involved in the teachings herein.

Epitope: The term "epitope" generally relates to a distinctive part of an antigen molecule that is specifically recognized by an antibody. The epitope of an antigen binds with its antibody in a highly specific interaction, allowing an antibody to firmly bind to its unique antigen in the midst of the millions of different antigens and other molecules that make up a sample fluid or an entire organism.

Target Molecule: as used herein a "target molecule" generally relates to reagents that preferentially bind to a targeted biomarker, in comparison to other biomarkers potentially present in a sample. The targeted biomarker and target molecule comprise a binding pair, and either member of the pair can be used as the target-specific reagent in order to selectively bind to the other member of the pair. Examples of target and target-specific reagent pairs include, but are not limited to, antigens and antigen-specific antibodies, hormones and hormone receptors, haptens and anti-haptens, biotin and avidin or steptavidin, enzymes and enzyme cofactors, lectins and specific carbohydrates thereof, ligands and receptors, and like binding complements. Capture molecules and biomarker conjugates can be the same or similar to the detection molecules and biomarker conjugates provided herein, and vice versa. Preferred target molecules include one or more antibodies, or fragments thereof, that include an antigen binding site that specifically binds (e.g., immunoreacts with) the biomarker antigen.

Capture Molecule: The term "capture molecule" as used herein generally relates to antibodies, antigens, enzymes, enzymatic substrates, ligands, receptors, bio-engineered scaffold proteins, synthetic nucleic acid (such as single-strand DNA or RNA) or other suitable biological molecules capable of covalently coupling to the solid O-ring support substrate and exclusively binding to a unique part, or an epitope, of a biomarker co-present with other countless biomarkers in a sample fluid. In general, certain teachings herein are directed to providing 1 or more O-rings having uniform shape and size, or substantially so, and are configured to act as solid supports to couple with 1 or more target-specific capture molecules.

Detect Molecule: The term "detect molecule" as used herein also generally relates to antibodies, antigens, enzymes, enzymatic substrates, ligands, receptors, bio-engineered scaffold molecule (preferred as proteins), synthetic nucleic acid (such as single-strand DNA or RNA), or other suitable biological molecules capable of directly binding to a unique part or an epitope of biomarker that is captured by or coupled to an O-ring and also covalently conjugating an enzyme or detectable tag (biotin, fluorescence, etc), or providing a unique part of itself as exclusive epitope recognized by the secondary detect molecule (preferably antibody). According to the teachings herein, after the capture-molecule on the O-ring binds the targeted biomarkers present in a sample, or after the total proteins of a sample is coupled to an O-ring, an individual detect molecule (e.g., antibody, Streptavidin-conjugated-enzyme, etc) is added to a specific biomarker captured onto or coupled to an O-ring. In the teachings herein, the term "detect molecule" is one of several major but non-exclusive categories of molecules: such as biotin-labeled or non-labeled antibodies if the biomarker is not conjugated with any recognizable tag, or Streptavidin-conjugated Alkaline-phosphatase (AP), Streptavidin-conjugated horseradish peroxidase (HRP) if the biomarker is prior conjugated with biotin tag. Others such as Streptavidin-conjugated Fluorescent tag can be used but not preferred herein.

Primary Detect Antibody: The term "Primary Detect Antibody" generally refers to antibody that is used to directly bind to a unique part or an epitope of the targeted biomarker captured by or coupled to the support substrate of O-ring Array and also to covalently conjugate with common detectable tag (such as biotin, fluorescence, etc), or an enzyme (such as AP, HRP), or to provide a unique part of itself as exclusive epitope recognized by the secondary detect molecule (including antibody). According to the teachings herein, after the capture-molecule on the O-ring binds the targeted biomarker present in a sample, or after the total proteins of a sample are coupled to an O-ring, a detect molecule (e.g., antibody, Streptavidin-conjugated-enzyme, etc) can be added to bind to a specific biomarker captured onto or coupled to an O-ring.

Secondary Detect Antibody: The term "Secondary Detect Antibody" generally refers to an antibody that is covalently conjugated with a detectable tag (such as biotin, fluorescent molecule, etc), or an enzyme (such as AP, HRP, etc) and also used to identify the primary detect-antibody that has already formed a complex with the targeted biomarker. According to the teachings herein, the secondary detect-antibody is advantageous when the primary detect-antibody is not labeled with any common detectable tag or enzymes for signal development and quantification.

Signal Generating Enzyme: The term "Signal Generating Enzyme" is one of several major but non-exclusive categories of molecules and their conjugated complex, such as horseradish peroxidase (HRP), Alkaline-phosphatase (AP), etc. According to the teachings herein, HRP and AP are the most commonly used enzymes in the Enzyme-Linked-ImmunoSorbent-Assay (ELISA) for the traditional single biomarker quantification.

Cytokine: The term "Cytokine" refers to a category of signaling molecules that are used extensively in cellular communication. They can include proteins, peptides, or glycoproteins. The term "cytokine" encompasses a large and diverse family of polypeptide regulators that are produced widely throughout the body by cells of diverse embryological origin. Historically, the term "cytokine" has been used to refer to the immunomodulating agents (interleukins, interferons, etc.). Some cytokines (such as IL-6) circulate in picomolar ($10^{-12}$) concentrations that can increase up to 1,000-fold during trauma or infection. Virtually all nucleated cells, but especially endo/epithelial cells and resident macrophages (many near the interface with the external environment) are potent producers of IL-1, IL-6, and TNF-α. The action of cytokines may be autocrine, paracrine, and endocrine. Cytokines are helpful to the development and functioning of both the innate and adaptive immune response, although not limited to just the immune system. They are often secreted by immune cells that have encountered a pathogen, thereby activating and recruiting further immune cells to increase the system's response to the pathogen. Cytokines are also involved in several developmental processes during embryogenesis.

Anti-inflammatory cytokines: a general term for the immuno-regulatory cytokines that counteract various aspects of inflammation, for example cell activation or the production of pro-inflammatory cytokines, and thus contribute to the control of the magnitude of the inflammatory responses in vivo. These mediators act mainly by the inhibition of the production of pro-inflammatory cytokines or by counteracting many biological effects of pro-inflammatory mediators in different ways. The major anti-inflammatory cytokines are IL4, IL10, and IL13. Other anti-inflammatory mediators include IL16, IFN-alpha, TGF-beta, IL1ra, G-CSF, as well as soluble receptors for TNF or IL6. It should be noted that the common and clear-cut classification of cytokines as either pro-anti-inflammatory or pro-inflammatory may be misleading. The net effect of an inflammatory response is determined by the balance between pro-inflammatory cytokines and anti-inflammatory cytokines. The type, duration, and also the extent of cellular activities induced by one particular cytokine can be influenced considerably by the nature of the target cells, the micro-environment of a cell, depending, for example, on the growth and activation state of the cells, the type of neighboring cells, cytokine concentrations, the presence of other cytokines, and even on the temporal sequence of several cytokines acting on the same cell.

Pro-inflammatory cytokines: a general term for those immuno-regulatory cytokines that favor inflammation. The major pro-inflammatory cytokines that are responsible for early responses are IL1-alpha, IL1-beta, IL6, and TNF-alpha. Other pro-inflammatory mediators include LIF, IFN-gamma, OSM, CNTF, TGF-beta, GM-CSF, IL11, IL12, IL17, IL18, IL8 and a variety of other chemokines that chemoattract inflammatory cells. These cytokines either act as endogenous pyrogens (IL1, IL6, TNF-alpha), up-regulate the synthesis of secondary mediators and pro-inflammatory cytokines by both macrophages and mesenchymal cells (including fibroblasts, epithelial and endothelial cells), stimulate the production of acute phase proteins, or attract inflammatory cells. The net effect of an inflammatory response is generally determined by the balance between pro-inflammatory and anti-inflammatory cytokines. It should be noted that the common and clear-cut classification of cytokines as either pro anti-inflammatory or pro-inflammatory may be misleading. The type, duration, and also the extent of cellular activities induced by one particular cytokine can also be influenced considerably by the nature of the target cells, the micro-environment of a cell, depending, for example, on the growth and activation state of the cells, the type of neighboring cells, cytokine concentrations, the presence of other cytokines, and even on the temporal sequence of several cytokines acting on the same cell.

Chemokine: Chemokines generally relate to a family of small cytokines, or proteins secreted by cells. Proteins are classified as chemokines according to shared structural characteristics such as small size (they are all approximately 8-10 kilodaltons in size), and the presence of four cysteine residues in conserved locations that are key to forming their 3-dimensional shape. Their name is derived from their ability to induce directed chemotaxis in nearby responsive cells; they are chemotactic cytokines. However, these proteins have historically been known under several other names including the SIS family of cytokines, SIG family of cytokines, SCY family of cytokines, Platelet factor-4 superfamily or intercrines. Some chemokines are considered pro-inflammatory and can be induced during an immune response to promote cells of the immune system to a site of infection, while others are considered homeostatic and are involved in controlling the migration of cells during normal processes of tissue maintenance or development. Chemokines are found in all vertebrates, some viruses and some bacteria, but none have been described for other invertebrates. These proteins exert their biological effects by interacting with G protein-linked transmembrane receptors called chemokine receptors, which are selectively found on the surfaces of their target cells.

Growth Factor: The term "growth factor" generally relates to a naturally occurring substance capable of stimulating cellular growth, proliferation or cellular differentiation. Usually it is a protein or a steroid hormone. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis) and system cells (e.g., lymphocytes and tissue cells from spleen, thymus, and lymph nodes). For the circulatory system and bone marrow in which cells can occur in a liquid suspension and not bound up in solid tissue, it makes sense for them to communicate by soluble, circulating protein molecules. However, as different lines of research converged, it became clear that some of the same signaling proteins the hematopoietic and immune systems used were also being used by all sorts of other cells and tissues, during development and in the mature organism. While growth factor implies a positive effect on cell division, cytokine is a neutral term with respect to whether a molecule affects proliferation. While some cytokines can be growth factors, such as G-CSF and GM-CSF, others have an inhibitory effect on cell growth or proliferation. Some cytokines, such as Fas ligand are used as "death" signals; they cause target cells to undergo programmed cell death or apoptosis.

Receptor: In biochemistry, a receptor generally relates to a protein molecule, embedded in either the plasma membrane or cytoplasm of a cell, to which a mobile signaling (or "signal") molecule may attach. A molecule which binds to a receptor is called a "ligand," and may be a peptide (such as a neurotransmitter), a hormone, a pharmaceutical drug, or a toxin, and when such binding occurs, the receptor goes into a conformational change which ordinarily initiates a cellular response. However, some ligands merely block receptors without inducing any response (e.g. antagonists). Ligand-induced changes in receptors result in physiological changes which constitute the biological activity of the ligands.

O-rings

Figure 1A:
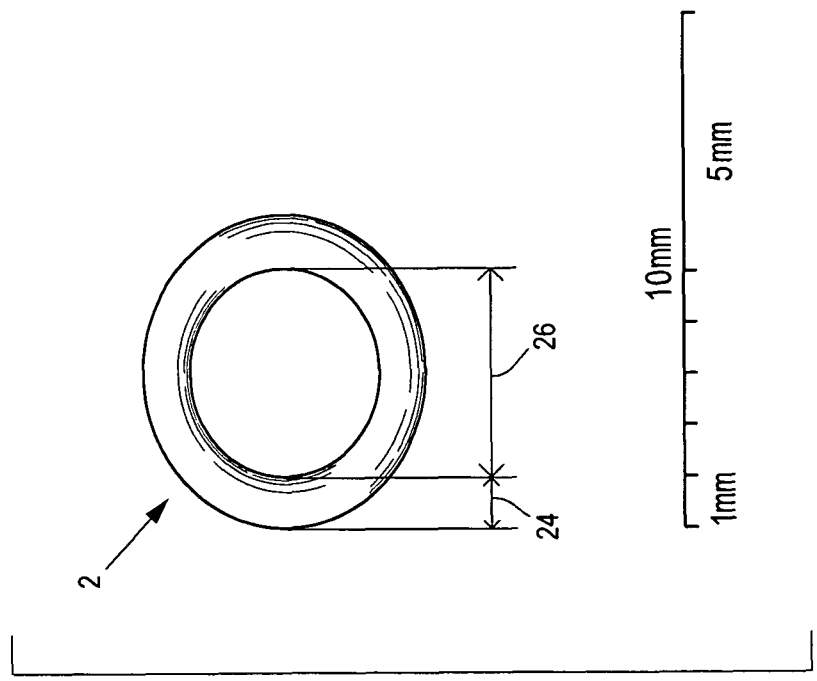
FIG. 1A depicts an O-ring.

The teachings herein relate to an array of O-rings 2 covalently coupled with one or more biomarker-specific capture antibodies, other high affinity capture molecules, or to biomarkers. According to certain embodiments, and as depicted in FIG. 1A, the O-rings 2 can be in the shape of a ring, or toroid, and are configured to rest within a well, such as tightly in the bottom of the well, of a standard 96 or 384 well microplate. Preferred sizes of ring-shaped O-rings 2 include those having an internal diameter 26 of 4 mm and a cross-section 24 of 1 mm. Other sizes of ring-shaped O-rings are also readily contemplated non-exclusively including smaller sized rings having an internal diameter of 1.5 mm and a cross-section of 1 mm. According to other embodiments, the term O-ring can relate to three-dimensional shapes other than rings or toroids. For example, an O-ring can non-exclusively be spherical, cubical, cuboidal, conical, cylindrical, pyramidal, prism-shaped, or ellipsoidal, for example. FIG. 1B depicts multiple, non-exclusive shapes of O-rings 2a-2i. O-rings have an opening, preferably in the center, and is configured to allow a probe, or pin, to pass through. Preferred O-rings can be configured in size to be fitted into any suitable well on a microplate, and/or to have an aperture that can be threaded by any suitable pin on a pin plate. According to more specific embodiments, an O-ring is a symmetrical 3-D shape having an aperture running through the central axis of the body. While O-rings 2 in a ring shape will be primarily discussed herein, those with skill in the art will readily recognize that other shapes of O-ring can readily be interchanged with them, where suitable.

O-rings 2 can be made of any appropriate material suitable for coupling to a capture molecule, or biomarker, including, but not limited to polymers such as polystyrene, which contains other co-polymers such as divinylbenzene; polymethylmethacrylate (PMMA); polyvinyltoluene (PVT); copolymers such as styrene/butadiene, styrene/vinyltoluene, and latex. Examples of other polymers that can be used to make the O-rings can non-exclusively include large molecules (macromolecules) composed of repeating structural units typically connected by covalent chemical bonds, including Bakelite, neoprene, nylon, polyvinyl chloride(PVC), polystyrene, polyacrylonitrile, polyvinyl butyral (PVB), silicone, and fluoropolymer, or fluoroelastomer, for example. In the teachings herein, fluoroelastomer is preferably utilized as the solitary composition of O-rings due to the high resistance of fluoroelsatomer to friction, low and high temperature, corrosive chemicals and organic solvents.

While dissimilar shaped and sized O-rings could be utilized herein, they are not-preferred. More specifically, the utilization herein of solid O-rings having uniform shape and size, or substantially so, greatly retains the fundamental principles and procedures of traditional Dual-Antibody-Sandwich Enzyme-Linked Immunosorbent Assay (DAS-ELISA) in the quantification of multiplex biomarkers in multiple samples. Unlike planar slide and bead-based microarrays, the O-ring arrays of this invention also adapt almost exactly the same apparatuses and instrumentation used by the traditional DAS-ELISAs in order to achieve similar reliability, accuracy, reproducibility, sensitivity and specificity in the qualification and quantification of multiplex biomarkers in multiple small volume samples, or large volume samples.

In general, the teachings herein are directed to providing 1 or more O-rings 2 having uniform shape and size, or substantially so, and are configured to act as solid supports to couple with 1 or more target-specific capture molecules, or biomarkers.

Methods of Using O-rings

General

In general the O-rings 2 provided herein, along with their bound capture molecules 12 (e.g., capture antibodies) are useful in detecting a number of different types of specific biomarkers 14 in a sample or standard fluid. O-rings 2 can also bind to biomarkers without the use of capture molecules 12, such as through SAD ELISA. O-rings 2 are preferably coated with a coupling reagent to facilitate binding to biomarkers 14 and/or capture molecules 12. The detection of biomarkers 14 bound to the capture molecules 12 or O-rings 2 can be performed using any suitable means available.

To provide some non-exclusive examples of biomarkers 14 capable of being captured and detected utilizing the teachings herein, Table 1 below displays 254 gene codes for the most active cytokines, cheomkines, angiogenic factors, growth factors and their soluble receptors circulating in human biological fluid systems. The systems and methods herein expressly allow for the detection and quantification of each of these biomarkers and many other any additional targeted biomarkers. The O-rings herein can be used with any suitable Dual-Antibody-Sandwich ELISA kit, such as those available for detecting the 254 biomarkers provided in Table 1, which are provided by R&D Systems, Inc. (614 McKinley Place NE, Minneapolis, Minn. 55413, USA), or any additional biomarkers ELISA kits developed by R&D Systems, Inc, or by others, available currently or in the future. In general, the currently available sandwich ELISA kits, which are chosen for the comprehensive profiling of cytokines and chemokines herein, are capable of detecting the presence of these biomarkers in quantities as low as 8 pg/milli-L-40 pg/milli-L. In a traditional ELISA assay, each of these kits can provide the linear dynamic ranges of quantification from 8 pg/milli-L or 40 pg/milli-L to 1000 pg/milli-L or 3000 pg/milli-L, for example.

TABLE #1

254 gene codes for the most active cytokines, cheomkines, angiogenic factors, growth factors and their soluble receptors circulating in human biological fluid systems.

| | 1 | 2 | 3 | 4 | 5 | 6 | 7 | 8 |
|---|---|---|---|---|---|---|---|---|
| 1 | Activin A | BMP-4 | CCL14a | CD14 | CXCL4 | Dkk-3 | E-Selectin | G-CSF R |
| 2 | ADAM9 | BMP-5 | CCL15 | CD23 | CXCL5 | Dkk-4 | Fas Ligand | GDF-15 |
| 3 | Adiponectin | BMP-6 | CCL16 | CD80 | CXCL6 | DLL1 | Fas | GDNF |
| 4 | AgRP | BMP-7 | CCL17 | CD97 | CXCL7 | DPPIV | Fc gamma RIIB | GITR Ligand |
| 5 | ALCAM | CA9 | CCL18 | CD200 | CXCL8 | DR6 | FGF basic | GITR |
| 6 | AREG | Cathepsin L | CCL19 | CD244 | CXCL9 | Dtk | FGF-4 | GM-CSF |
| 7 | Angiogenin | Cathepsin S | CCL20 | CEACAM-1 | CXCL10 | E-Cadherin | FGF-6 | gp130 |
| 8 | ANGPT1 | CCL1 | CCL21 | Chemerin | CXCL11 | EDA-A2 | FGF-9 | HAI-1 |
| 9 | Angpt2 | CCL2 | CCL22 | CNTF | CXCL12 | EGF | FLRG | HB-EGF |
| 10 | ANGPTL4 | CCL3 | CCL23 | C5AR1 | CXCL12 | EGF R | Flt-3 Ligand | HGF |

TABLE #1-continued 254 gene codes for the most active cytokines, cheomkines, angiogenic factors, growth factors and their soluble receptors circulating in human biological fluid systems.

| 1 | 2 | 3 | 4 | 5 | 6 | 7 | 8 |
|---|---|---|---|---|---|---|---|
| 11 Axl | CCL4 | CCL23 | CFD | CXCL13 | EG-VEGF | Furin | HVEM |
| 12 BCAM | CCL5 | CCL24 | CRP | CXCL14 | Endoglin | Galectin-3 | ICAM-1 |
| 13 BCMA | CCL7 | CCL25 | Cripto | CXCL16 | EpCAM | Galectin-7 | ICAM-3 |
| 14 BDNF | CCL8 | CCL26 | CRTAM | DAN | ErbB2 | Gas1 | IFN-gamma |
| 15 Betacellulin | CCL11 | CCL27 | CX3CL1 | Decorin | ErbB3 | GASP-2 | beta IG-H3 |
| 16 beta-NGF | CCL13 | CCL28 | CXCL1 | Dkk-1 | Erythropoietin R | G-CSF | IGFBP-1 |
| 17 IGFBP-2 | IL-13 R alpha 1 | IL-22 | LAG-3 | MMP-8 | PDGF-BB | TGF-b 1 | TSLP |
| 18 IGFBP-3 | IL-13 R alpha 2 | IL-24 | Layilin | MMP-9 | Pentraxin 3 | TIM-1 | Ubiquitin + 1 |
| 19 IGFBP-4 | IL-15 | IL-27 | Leptin | MSP | PlGF | TIMP-1 | PLAUR |
| 20 IGFBP-5 | IL-16 | IL-28A | LIF | NCAM-1 | Prolactin | TIMP-2 | PLAU |
| 21 IGFBP-6 | IL-17 | IL-29 | LIGHT | Nidogen-1 | RAGE | TIMP-3 | VCAM-1 |
| 22 IGF-I | IL-17 R | IL-3 | LIMPII | NOV | RANK | TIMP-4 | VEGF |
| 23 IGF-I R | IL-17B | IL-31 | Lipocalin-2 | NrCAM | SCF | TNF RI | VEGF R1 |
| 24 IL-1 alpha | IL-17C | IL-33 | LOX-1 | NRG1-b 1 | SCF R | TNF RII | VEGF R2 |
| 25 IL-1 beta | IL-17D | IL-4 | L-Selectin | NT-3 | Serpin A4 | TNF-a | VEGF R3 |
| 26 IL-1 RI | IL-17F | IL-5 | LYVE-1 | NT-4 | Serpin E1 | TNF-b | VEGF-C |
| 27 IL-1 RII | IL-18 BPa | IL-6 | Marapsin | OSM | sFRP-3 | 4-1BB | VEGF-D |
| 28 IL-10 | IL-18 | IL-6 R | MBL | GPNMB | Siglec-5 | TRAIL R3 | WIF-1 |
| 29 IL-11 | IL-1ra | IL-7 | M-CSF | SPP1 | Siglec-9 | TRAIL R4 | XCL1 |
| 30 IL-12 p70 | IL-2 | Kallikrein 14 | M-CSF R | TNFSF11 | ST2L | TRAIL | XEDAR |
| 31 IL-12 | IL-2 R alpha | Kallikrein 3 | MICA | P-Cadherin | TACE | TWEAK | |
| 32 IL-13 | IL-20 | KGF | MICB | PDGF-AB | TGF-a | Trappin-2 | |

Additional embodiments are directed to allowing a multi-layer O-ring matrix to mix with a sample or standard fluid and allowing affinity chromatography to concentrate and isolate the multiplex biomarkers from the sample or standard fluid onto the capture molecules coupled to the O-rings. Still further embodiments are directed to means for sorting and transferring the O-rings for testing, analysis, and replacing their bound substances.

Additional embodiments are directed to configuring the O-rings herein into an array to analyze multiple samples and standard curves in parallel. Further methods herein allow O-rings having the same biomarker-specific capture molecule-coupled to them, to be individually mixed with different samples or standard (known solutions) and placed into the same row or column of wells of the same micro-plate, and even more preferably in adjacent wells. This can be done by placing a single O-ring per well in an ELISA plate and thereby allowing for reliable quantification. To provide one non-exclusive example, a $1^{st}$ microplate row can include the following adjacent wells: O-ring 1 coupled to a capture molecule A and mixed with sample X, O-ring 2 coupled to capture molecule A and mixed with sample Y, and O-ring 3 coupled to capture molecule A and mixed with sample Z, and so on. Likewise the $2^{nd}$ mircoplate row (positioned next to the first row) can include the following adjacent wells: O-ring 1' coupled to a capture molecule B and mixed with sample X, O-ring 2' coupled to capture molecule B and mixed with sample Y, and O-ring 3' coupled to capture molecule B and mixed with sample Z, and so on. Alternatively, microplate rows can be readily interchanged with columns.

After the O-rings are placed in their individual wells, detect molecules (e.g., detect antibodies) configured to probe the specific biomarker captured on the sorted and isolated O-rings can be added to the row of wells. Adding only one type of detect molecule to a row or column of isolated O-rings ameliorates the signal cross-talking and noisy background and thus improves the specificity of detection. After admixing, the detection molecules, the sorted and isolated O-rings can be washed and the signaling products of the sample(s) and standard(s) can be generated by enzymatic activity and detected simultaneously in parallel. More specifically, the concentration of the captured biomarker in a homogeneous solution can be determined through spectrometry, such as in traditional DAS-ELISA, to maintain the accuracy, reproducibility and sensitivity of quantification.

According to further methods, the materials and methods herein can allow a researcher to carry out reverse ELISA arrays to comparatively quantify high multiplex biomarkers in multiple samples. For these methods, the proteins or biomarkers of each sample are covalently coupled to a set of O-ring arrays at a ratio of one protein/biomarker per each O-ring. Two or more groups of samples can be simultaneously set up and probed in parallel with thousands of antibodies available from commercial and proprietary sources. The quantification of the biomarkers among each sample is highly similar in statistical analysis due to the fact that all of samples are similarly and simultaneously processed in parallel.

Because proteomic components in circulating biological fluid systems provide the greatest potential for researches to learn more about human diseases, therapeutic responses, and health status, the presented methods and material herein can provide the most comprehensive and powerful proteomic platform to reveal the underlying mechanism of many diseases, drug efficacy and toxicity, and environmental exposures. Particularly the teachings herein make it possible for clinicians to effectively diagnose disease status, predict disease outcome, and individualize medicinal strategy while avoiding adverse effect of drug and other therapeutics, based upon the comprehensive proteomic profiles of patients.

The teachings herein allow for a variety of quantitative proteomic analyses beyond those described above. For example, methods and devices are described herein to allow a researcher to accurately quantify 384 biomarkers in multiple small volume samples simultaneously in parallel. According to certain embodiments, the number of volume samples can be a multiple of 384, such as 8, 16, 32, for example, or other suitable numbers Dual-Antibody-Sandwich (DAS)—ELISA O-Ring Array The term "dual-antibody-sandwich ELSIA (DAS-ELISA) O-ring Array", refers to an array of a predetermined number of solid uniform shaped and sized, or substantially so, O-rings, each of which is coupled with a different capture molecule (e.g., antibody) capable of binding to a specific part of a particular targeted biomarker in a sample or standard fluid. While DAS, SAC, and SAD ELISA assays traditionally rely on antibodies, the teachings herein are broader and cover any suitable capture molecules and detect molecules, whether antibodies or not. The DAS-ELISA arrays herein also allow a particular detect molecule to bind to another specific part of the same targeted biomarker. A general overview of a DAS-ELISA O-ring Array is provided in FIG. 2. Additionally, the methods and instrumentation provided below, including means for incubating the O-rings 2 with sample or standard fluid, means for sorting, and transferring the O-rings 2 to microplates or other suitable containers, and means for detection, can be utilized with other methods, where suitable, non-exclusively including SAC-ELISA and SAD-ELISA O-ring arrays, for example.

According to the teachings herein, a plurality of different capture molecule coupled O-rings 2 can be anchored through a pin, or a probe, in a pre-arranged sequential position and tightly packed into a well (including a deep well) of microplate, or a cylindrical tube to form a short or long multi-layer O-rings immuno-affinity chromatography column. Based upon the size of samples and the number of standard controls, each of the multi-layer O-rings immuno-affinity chromatography columns can be prepared the same, or substantially so. According to more preferred embodiments, any one of the O-rings 2 coupled with a same specific capture molecule 12 can be advantageously placed in the same sequential position within each of multi-layer O-rings immuno-affinity chromatography columns. Each of the multi-layer O-rings immuno-affinity chromatography columns is capable of capturing and isolating the multiplex biomarkers present in a sample, or standard fluid, when fully exposed to or incubated with the sample or standard fluid. As an example, any number, from 1 or up to hundreds of O-rings 2 can be positioned into a multi-layer O-rings immuno-affinity chromatography column used for the quantification of an equivalent number of different biomarkers in a sample or standard solution.

In order to utilize a DAS-ELISA O-ring Array to quantify multiplex biomarkers 14 in multiple samples, an equivalent number of identically-made, or substantially so, multi-layer immuno-affinity O-ring chromatography columns can be respectively set up for the same number of samples and standard controls. The equal volume of each sample and standard control can be loaded into one of identical multi-layer immuno-affinity O-ring chromatography columns, allowing the sample and standard control fluids to fully expose to each of the different capture molecule coupled O-rings 2 inside for the sufficient time. After incubation, each layer of O-rings 2 that couple with the same capture molecule can be sorted respectively out of all multi-layer O-rings immuno-affinity chromatography columns and placed in the same, or another tracked, order into the wells of the same ELISA microplate. This allows the O-rings 2 with same captured biomarker 14 from all samples and standard controls to form a unique O-ring Array in a microplate 20 that can be detected simultaneously, in parallel. Thus, one unique O-ring Array in an ELISA microplate can allow for the quantification of a unique biomarker in all samples and standard controls. According to certain embodiments, one standard ELISA microplate (such as 384-well Microplate) can house one or sixteen O-ring arrays for the quantification of one or sixteen biomarkers, in multiple samples, run simultaneously in parallel. According to further embodiments, any number from one or hundreds of ELISA microplates can be set up in a similar way to house one or hundreds of different O-ring arrays for the quantification of one or hundreds of targeted biomarkers in the multiple samples.

Figure 5:
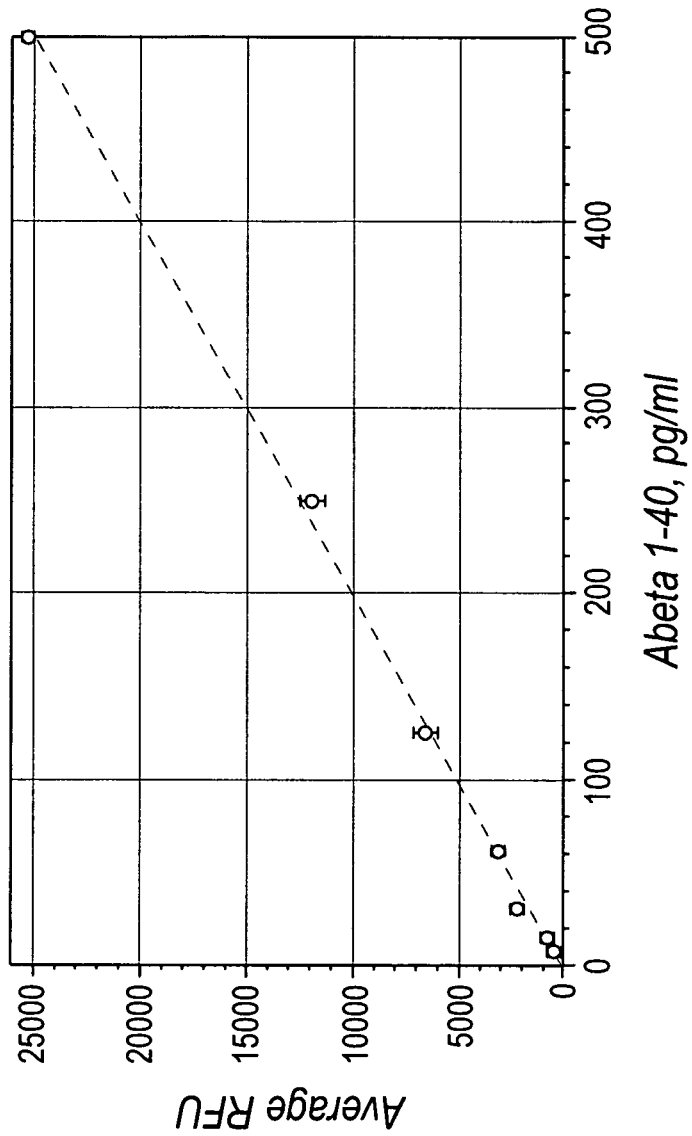
FIG. 5 depicts a standard curve generated from an ELISA Array

Preferably, the DAS-ELISA O-ring Arrays provided herein, can include standard controls, non-exclusively including, a series of 2-fold diluted concentrations of purified targeted biomarker molecule (provided by DAS-ELISA kit manufacturer) and blank controls free of targeted biomarker and that can include non-specific proteins used as the blocking proteins (e.g., casein, and bovine serum albumin) that are run simultaneously, in parallel throughout the assay. A standard curve can be generated for each set of targeted biomarker in a DAS-ELISA O-ring Array assayed. The graph provided in FIG. 5 represents typical data generated when using human Abeta 1-40 DAS-ELISA O-ring Array. A standard curve can be used to calculate the concentration of targeted biomarker in all sample fluids using any suitable means, including statistical software.

According to one non-limiting embodiment, the teachings herein provide a Dual-Antibody-Sandwich ELISA microarray for the quantification of 384-multiplex biomarkers in 8 small volume samples (e.g., 100 ul undiluted fluid mixed with detergent buffers 100 ul or maximal 400 ul). The following procedure can be done with any suitable number of O-rings 2 and any type plate. As a first step, 384 separate, but uniformly shaped and sized, solid O-rings 2 are provided and treated with a coupling agent 3, such as 3-glycidoxypropyltrimethoxysilane (3-GPS). Each individual O-ring 2 is then covalently coupled with a particular type of capture molecule 12 (e.g., capture antibodies), preferably to a plurality of the same type of capture molecules 12. Afterwards, each of the 384 O-rings 2 are coupled to their own specific type of capture molecule 12 designed to capture a particular biomarker 14 along its' three-dimensional surface. According to certain embodiments, each O-ring 2 will only be coupled to a plurality of one particular type of capture molecule 12; in other words there will not be different types of capture molecules 12 on the same O-ring 2. One different type of capture molecule 12 can be coupled to each O-ring 2. It is not necessary that each O-ring 2 contains 1 of 384 different types of capture molecules, and it is readily contemplated that different O-rings 2 can contain the same particular type of capture molecule 12.

Figure 3:
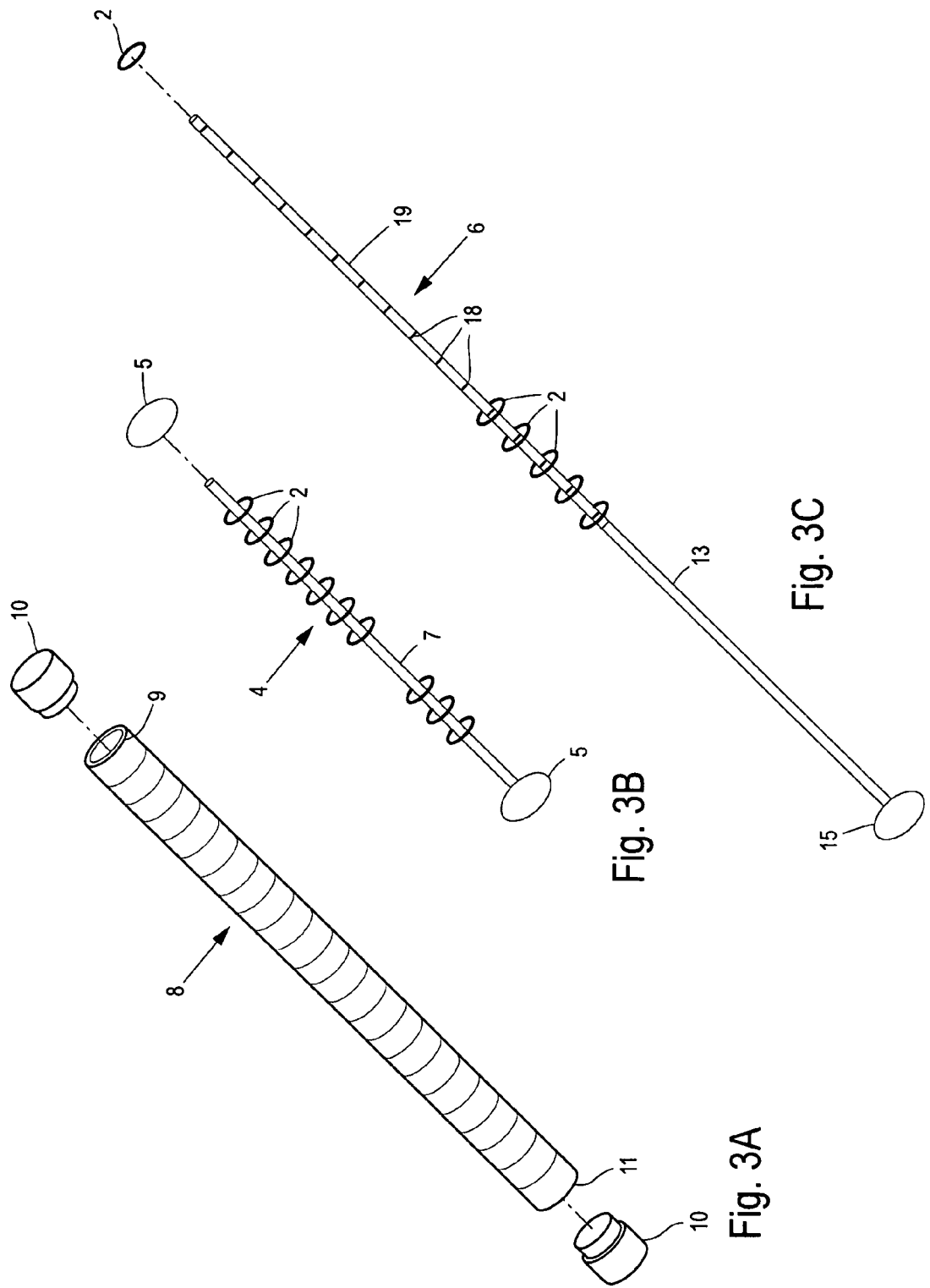
FIG. 3A depicts an O-ring container
FIG. 3B depicts an O-ring fixture probe.
FIG. 3C depicts an O-ring sorting probe.

A fixture probe 4, such as depicted in FIG. 3B, can be placed through the apertures of a group of O-rings 2 bound to their respective capture molecules 12, thereby aligning them. In more specific embodiments, the O-rings 2 are sequentially arranged in a predetermined order along the central body 7 of the fixture probe 4 and then placed into an O-ring container 8, or a well, configured for mixing a sample fluid (e.g., bodily fluid, blood sample, serum, and the like) with the O-rings 2. More specifically, and according to preferred embodiments, containers 8 are configured to allow a multi-layer O-ring 2 matrix to mix with a sample or standard fluid and allowing affinity chromatography to concentrate and isolate the multiplex biomarkers 14 from the sample or standard fluid onto the capture molecules 12 coupled to the O-rings 2. FIG. 3A depicts a preferred container 8. According to other embodiments, some or all of the O-rings 2 on the fixture probe are each individually coupled to a different capture molecule 12. According to other embodiments, some or all of the O-rings 2 arranged on a fixture probe 4 contain the same type of capture molecule 12 configured to bind with the same biomarker 14. It is preferred that each O-ring 2 and its coupled capture molecule 12 are known, and the O-rings 2 are sorted in a particular sequential order with one another that is maintained and tracked. If the sequential order of the O-rings 2 is not maintained, it should be trackable, such that a user can know which O-ring 2 is coupled to which capture molecule 12, and which sample or standard fluid it has been incubated with.

According to certain embodiments, the fixture probe 4 does not require multiple grooves or flanges along it central body 7 to retain each O-ring 2. To prevent excessive sliding, the diameter or the central body 7 of the fixture probe 4 can be slightly shorter than the diameter of the internal diameter 26 of the O-rings 2, such as 0.1-0.2 mm shorter, or substantially so, for example. For use with O-rings having internal diameters of 4 mm and 1.5 mm fixture probes can have cross-sectional diameters at approximately 3.9 or 3.8 mm or 1.4 or 1.3 mm respectively. For fixture probes that are not cylindrical in shape, it is readily contemplated that the width of the probe's cross section is only slightly smaller than the width of the aperture in the O-ring 2. Additionally, the fixture probe 4 can include a retainer 5 positioned at, or near, the end of the central body 7 and having a larger cross-section than said body 7. Preferably the retainer 5 is small enough to fit within the container 8 and may be permanently or removably attachable to the probe 4. A second, similarly sized, retainer 5 can also be added to the other end of the fixture probe. According to most embodiments, the 1 or 2 retainers 5 can be configured to be removably attached to the fixture probe. For example, after O-rings 2 are placed on a fixture probe 7 with a single retainer 5, a second retainer 5 can be added to the opposite end of the fixture probe 7.

The O-ring container 8 can be an elongated container, and can be in the shape of a cylinder, for example, such as depicted in FIG. 3A. Other shapes of containers can be used to accommodate different sized and shaped O-rings 2. According to certain embodiments, the O-ring container 8 does not need flanges or grooves to hold the O-rings 2 in their arranged order. According to more specific embodiments, the outer diameters of the O-rings 2 are slightly shorter than the inner diameter of the O-ring container 8, such as 0.5 mm shorter, for example, to allow for a tight fit within the container 8. The distance from an O-ring 2 to the inner wall of the container 8 should be at a short enough distance such that the O-rings 2 are substantially prevented from migrating away from their pre-arranged positions. Other means of maintaining the O-ring order while they are mixed with a sample fluid are also contemplated, and non-exclusively include the use of grooves, flanges and leaving the fixture probe 4 in the container 8 during the admixing. When the fixture probe 8 is threaded through the apertures of the O-rings 2, is retained in the container 8 during the incubation with the sample fluid, it is preferred that the fixture probe 8 is configured to be a length that fits within the sealed container 8.

The container 8 can include means for allowing O-rings 2 to be removed and added with the sample or standard fluid, and thus can include one or two openings, for example. As shown in FIG. 3A, the container can include a first and second opening 9 and 11, that can be positioned at the ends of the container 8. The openings 9 and 11 can be configured to be fluidly sealed and unsealed using suitable plugs 10, or other means.

A sample fluid can be mixed with the arranged O-rings 2 inside of the O-ring container 8 using any suitable means. According to one embodiment, with one end 11 sealed with a plug 10, a lab pipette is used to transfer sample fluid into the container 8 through the unsealed opening 9. The opening 9 can then be sealed with a plug 10, thereby entirely sealing the arranged O-rings 2, their capture molecules 12, and their fixture probe 4 within the entire container 8.

The length of both tubing container 8 and fixture probe 4 can then be suitably shortened using any suitable means, including precise cutting tools specific for plastic tubing and metal wire, for example. It can also be advantageous to cut such that the tubing or probe ends are smooth; this can effectively allow the targeted biomarkers 14 in the fluid to bind with their respective capture molecules 12 on the O-rings 2. One such method of incubation includes fixing the container 8 at an upright, or vertical, position onto an automatic rotator and turning it vertically at 180° angle several times per minute. In certain embodiments, the container 8 can be rotated for 16 hours at 4° C. of temperature in order to allow the sample fluid to flow from one end of container 8 to the other utilizing gravity. The length of container 8 can be configured so that there is appropriate overhead space near both openings 9 and 11 to collect most of the sample fluid (such that it is not contacting the O-rings 2, or substantially so) during each cycle of vertical rotation. This particular configuration allows most of the, or near the entire, sample fluid to traverse the length of the container 8 thus allowing exposure to each O-ring 2. This space will depend on the length of the container 8, fixture probe 4, and the amount of sample fluid, but according to certain embodiments, there can be about 30-50 mm in length from the last O-ring 2 to the sealing plug 10.

After the incubation of sample fluid with the O-rings 2, the one or more plugs 10 can be removed from the container's one or more openings 9 and 11. While it is possible for the fixture probe 4 to be used to transfer the O-rings 2 to the wells 22 in a micro-plate 20, according to more preferred embodiments, a longer sorting probe 6 can be used to extract the O-rings 2 from the container 8 after the admixing with the sample solution. The sorting probe 6 includes a central body 13 and can include a removable flange-like, or other type of retainer 15 having a larger diameter than the body 13 but small enough to fit within the container 8. The central body 13 of the sorting probe 6 is configured to traverse through the apertures of the O-rings 2. According to certain embodiments, the sorting probe 6 includes an extended section 19, positioned at the opposite end of the main body 13 from the retainer 15 end. The sorting probe 6 can be longer than the fixture probe 4 and longer than the container 8, such that the extended section 19 can facilitate the transfer of O-rings 2 along the length or width of a standard 96 or 384 well microplate, such as about 75 millimeters longer, for example. The longer body 13 can also allow a user to grip the sorting probe 6 or the container 8 holding the sorting probe 6 without coming into contact with the sample fluid, and the extra length makes it easier to release the O-rings 2 into their respective wells 22 on the plate 20. The sorting probe 6 can work similarly to the fixture probe 4 but preferably includes more defined means for securing and releasing the arranged O-rings 2 into wells. More specifically, the sorting probe 6 can include one or more grooves 18, wherein the grooves 18 are configured to releasably hold an O-ring 2. For example, if 16 O-rings 2 were admixed with the sample solution in the container 8, it is preferred that the sorting probe 6 included at least 16 grooves 18 for extracting said O-rings 2 from the sample solution while maintaining their established order, or reverse order, along the sorting probe 6. According to further embodiments, the grooves 18 are positioned on the extended section 19 of the sorting probe 6. Advantageously, the grooves 18 on the sorting probe 6 are the same, or substantially the same, distance from one another as the distance between adjacent wells in a row on a standard 96 or 384-well microplate.

Figure 4:
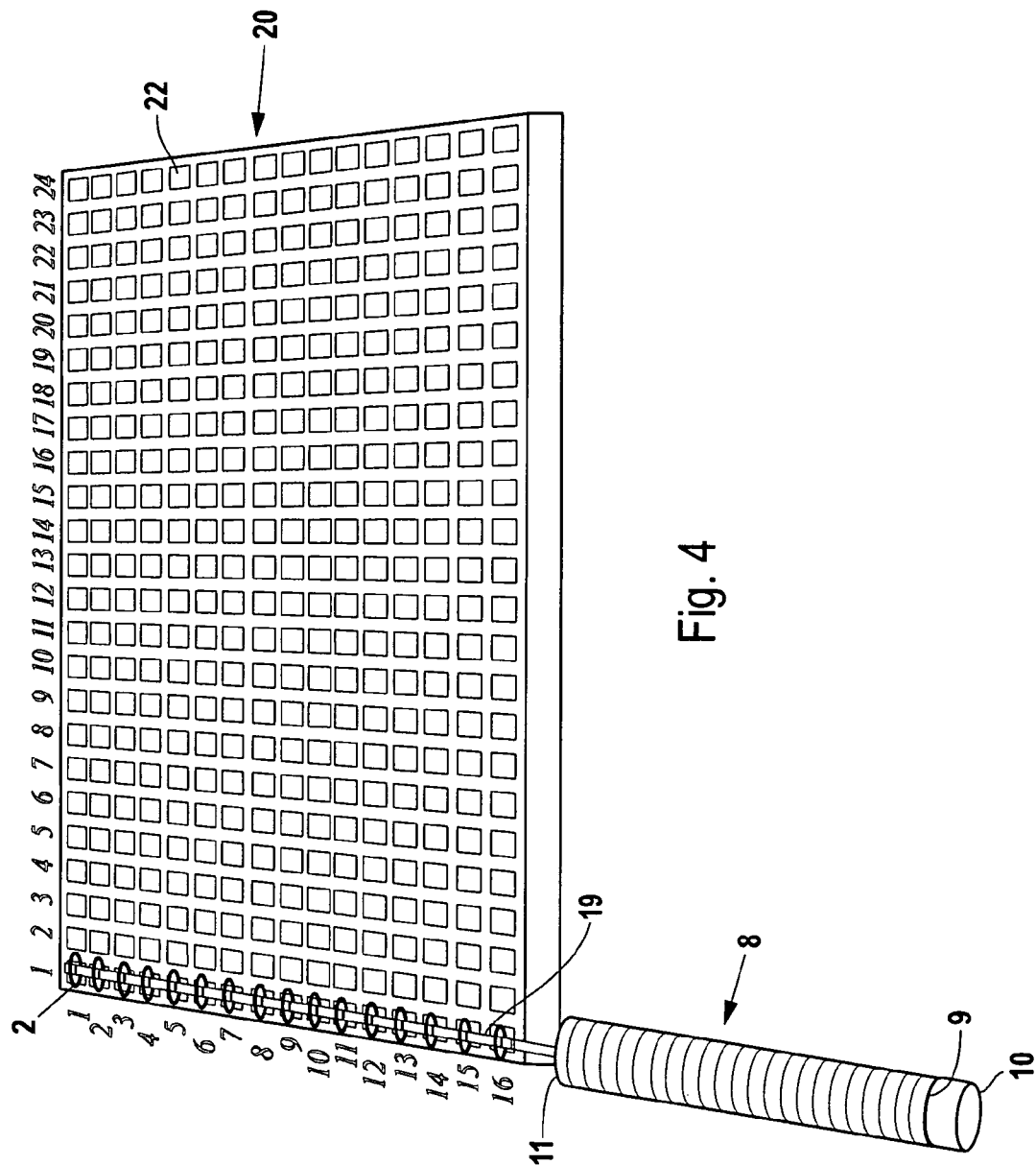
FIG. 4 depicts O-rings being arranged into a 384 well microplate

According to certain embodiments, means are provided for transferring the O-rings 2 from the Multi-Layer O-ring Affinity Chromatography Column Container, such as the tubing container 8 used for housing potentially over hundreds of O-ring layers, into a standard ELISA microplate 20 after the incubating of sample fluid with the O-rings 2. According to certain methods, a first plug 10 is removed from the container at a first end 9 and the sample fluid is drained from the container 8. This should not cause the O-rings 2 within the container 8 to dry out. A retainer 5 on the fixture probe 6 near the first end 9 can be removed. The second plug 10 positioned at the second end 11 of the container 8 can be removed. The extended section 19 of the sorting probe 6 can be pushed through the first opening 9 of the container 8, against the end of the fixture probe's main body 7 that no longer includes the retainer 5 such that the fixture probe 4 is pushed out of the container 8 at its' second end 11. The fixture probe 4 is pushed until the sorting probe 6 replaces the fixture probe 4 through of the apertures of the O-rings 2. According to certain embodiments, during this process the O-rings 2 can be gripped with a tool (e.g., sharp forceps) such that they are prevented from moving with the fixture probe 4 and allow the fixture probe 4 to slide through between its two arms. When the sorting probe 6 completely replaces the fixture probe 4 inside the centers of all O-rings 2, a retainer 15 can be placed on the end of sorting probe 6 at the opposite end of the extended section 19 and pushed inside the container 8 at the first end 9. The first end 9 of the container 8 can then be sealed with a plug 10. In this configuration, the extended section 19 of the sorting probe is exposed outside the container 8 through the second end 11. This configuration allows the container 8 to be held as a handle with the sorting probe 6 partially inside and partially outside of the container 8 as shown in FIG. 4. According to certain embodiments, the O-rings 2 can be positioned into their respective grooves 18 on the extended section 19 through any suitable means. One such way would be to use sharp forceps to pull the O-rings 2 out of the container along the body 13 of the sorting probe 6 to their grooves 18, such that their sequential order is maintained. Once the O-rings 2 are positioned in their respective grooves 18 along the extended section 19 of the sorting probe 6, they are ready for transfer of to the wells 22 of a microplate 20.

The above method simply describes a preferred way of incubating O-rings 2 with a sample fluid and transferring them to a microplate 20. Those with skill in the art will readily acknowledge other means for incubating the O-rings 2 with sample fluid, sorting said O-rings 2, and transferring to a microplate 20. Said means can be either manual or automated. Preferred means for sorting and transferring the O-rings 2 are members, such as probes, configured to traverse through the O-ring's apertures. Other means for sorting and transferring the O-rings 2 that do not traverse through the O-ring's apertures are also contemplated and can non-exclusively include pipettes or other suction devices, whether manual or automated. Additionally, it is preferred that said sorting and transferring means maintain the predetermined sequential order of the O-rings 2 during incubation and/or transfer to the microplate.

Configuring grooves 18 on the sorting probe 6 such that they are spaced at intervals equal to the distance between wells 22 on the microplate 20 allows a user to easily align O-rings 2 over the wells 22 for easy transfer. The number of grooves 18 on the sorting probe can vary depending on how many O-rings 2 the user wishes to transfer to wells. The sorting probe 6 can be configured to transfer an O-ring 2 to each well 22 in a row or in a column on any suitable microplate 20. For example, as a 384 well microplate includes 16 rows×24 columns of wells, it is preferred that the sorting probe includes either 16 or 24 grooves 18, depending on whether the O-rings 2 are to be transferred to rows or columns. Of course it is not required to fill every well 22 in each row and column in a microplate 20, and a sorting probe 6 can include a smaller number of grooves or O-rings 2 than the number of wells 22 in a targeted row or column in a microplate 20. According to most embodiments only one O-ring 2 will be transferred to a particular well 22 in a microplate 20. Once the O-rings 2 positioned on the grooves 18 are aligned over the targeted wells 22, a user can rotate the sorting probe 8, and or use forceps, to transfer each O-ring 2 into its respective well 22.

As an example, and with respect to FIG. 4, the 16 O-rings 2 are individually held in their respective 16 grooves 18, they are aligned above the respective 16 wells comprising a column of a standard 384 well microplate 20 (16 wells×24 wells) and released into their wells 22. Accordingly, 16 wells in each column individually contain one of the 16 O-rings 2, each of which is coupled with the different type of capture molecule 12 and has been incubated with the same sample or standard controls to allow binding with a target biomarker 14. This process can be repeated with the other columns of the microplate 20. A second group of 16 O-rings 2, having the same capture molecule 12 sequential order as the first group of O-rings 2, can be admixed with a second sample of fluid or a standard, using the tools and methods described above, and then can be placed into a second column of wells 22 on the same microplate 20, adjacent to the first column.

By repeating this procedure, the 24 wells in each row of 384 well microplate 20 can individually contain 1 of 24 O-rings 2 each of which is coupled with the same capture molecule 12 and each of which has incubated separately with different, or otherwise identifiable samples, or standard controls (including blank ones). The above process is simply provided for illustrative purposes only and those with skill in the art can readily utilize means for transferring the O-rings 2 such as a sorting probe 6 to place the O-rings 2 row by row into wells 22, instead of column by column. Thus, for example, a sorting probe 6 could include 24 grooves on the elongated section, for example. The numbers of O-rings 2 on the means for transferring, such as the sorting probe 6, can also vary depending on where they are being transferred to, such as the number of wells per row and column on the ELISA microplate 20.

In addition to microplate wells and containers (e.g., sealable tubes), it is also contemplated herein that a user can assemble or transfer the O-rings 2 onto pins 110 on a pin plate 100, such as a 96 or 384 pin microplate, where the pins 110 traverse through the apertures of the O-rings 2 to hold them in place. O-rings 2 can either be individually placed or stacked sequentially on a pin 110. Placing a single O-ring 2 per pin 110 can allow a user to quantify up to 384 different biomarkers, or as many biomarkers as there are pins 110 present on the pin plate 100. If a user wanted to quantify even more biomarkers they could sequentially stack a plurality of O-rings 2 on individual pins 110. FIGS. 9A, 9B, 10A, and 10B, show the sequential stacking of four O-rings 2 on an individual pin 110 on a 384 pin plate 100 for a total of 1536 O-rings 2 per pin plate 110. Of course not every pin 110 on a pin plate 100 necessarily has to have O-rings 2. A user can use fewer O-rings 2 as desired.

After the O-rings 2 (and their capture molecules) are threaded through the pins 110 they can be incubated with a sample or standard fluid by any suitable means. As one example as shown in FIG. 9A, the pin plate 100 can include side walls 120 configured to retain fluid when loaded on the pin plate 110. The walled 120 pin plate 100 can be sealed with a suitable lid 90, such as a single reservoir, devoid of individual wells. Alternatively, the O-rings 2 on a pin 110 can be secured with a ring retainer 130 on each pin 110, as non-exclusively shown in FIG. 10B, and the entire pin-plate 100 can be turned upside down to allow either all the pins 110 submerge into one-well standard reservoir plate 90. This particular method to submerge the pins 110 in one well reservoir plate 90 is advantageous when the available volume of sample fluid, is non-exclusively between about 4-8 mL, such as a human urinary sample, or cell culture media, and/or when there a low concentration of biomarkers in the sample fluid.

As another example of incubating a pin plate 110 with sample fluid, a standard polypropylene storage microplate 200 having as many wells 220 as there are pins 110 on the pin plate 100 can be utilized as storage container to hold the O-rings 2 released from pin plate while keeping the O-rings 2 in the trackable order, as shown in FIG. 10A. Smaller and larger sized pin plates and corresponding well plates can also be used with these teachings, non-exclusively including a 96 pin plate and a 96 well microplate, for example. This configuration allows each pin 110 with one or more O-rings 2 to be submerged in each well 220 that has been pre-loaded with sample fluid, such as 50 micro-L of fluid. As the standard polypropylene storage microplate 200 can be placed upright, as shown in FIG. 10A, the pin plate 100 can turned upside down to be positioned into each well, such that the O-rings 2 are submerged in the sample or standard fluid, in the well 220. To prevent the O-rings 2 from sliding off the pin 110 when turned upside down, a retainer 130 can be placed on the pin 110 and removed when it is desirable to release the O-rings 2 into the wells 220. The retainer 130 can be a different sized O-ring (without a capture molecule) with a smaller internal diameter 26, or any type of flange, for example. Incubating the O-rings 2 on the pins 110 in individual wells is advantageous when there is a larger volume of sample fluid available, such as about 8-12 mL, and/or when there is a high concentration of biomarkers present in the fluids.

The two types of incubation described above can be carried out for at least 16 hours at 4° C. and on the orbit rotating shaker at 30 rpm. After incubation of the O-rings 2 with the sample fluid, the O-rings on the pin microplate 100 can be transferred for detection using any suitable means. As one example, the O-rings 2 can be released in the wells 220 of a standard polypropylene storage microplate 200. All O-rings 2 on any given pin 110 can be released into a well 220 the given pin 110 is placed into. This allows the O-rings 2 to be conveniently rearranged in ELISA microplates for the next procedural steps and prevents the O-rings 2 from drying-up and being contaminated in the open air. For example, if there were 4 O-rings on an individual pin 110, all 4 O-rings 2 could be released into the single well 220 the pin 110 was placed into. O-rings 2 can also be transferred from pin plates 100 using manual pipettes, automated multiple pipettes, or by forceps, for example.

As one example, 24 of 384-pin plates 100 can be set up for 8 samples, 7 two-fold diluted biomarker standards each in duplicate pin-plates and 1 blank controls in duplicate pin-plates, wherein each of 384-pin plate holds a total 1536 O-rings, wherein a set of 4 O-rings is sequentially stacked on each pin 110 and secured with a ring-retainer 130. Then, each of the 384-pin plates 100 wherein each includes the same volume of sample fluid, biomarker standard fluid, and blank control fluid are simultaneously shaken on an orbit shaker at 4° C. of temperature for 16 hours or so. Afterwards, all O-rings 2 on the 384-pin plate 100 can be respectively released into the wells 220 in a 384-well standard polypropylene storage microplate 200 to form 4 layers of O-rings 2 in each well 220. The O-rings 2 can then be rearranged into a 384-well ELISA microplate 20 that has been pre-coated with blocking protein using a multi-channel vacuum aspirator as FIG. 6. In order to probe, detect and quantify any given biomarker, all of the O-rings 2 with the same biomarker/capture molecule complexes from every 384-well standard polypropylene storage microplate 200 can be transferred and rearranged into the same 384-well ELISA microplate 20. This allows the same O-ring/capture molecule/biomarker complexes to be probed, detected and quantified simultaneously under the same processing condition for the samples, standard controls and blank control.

More specifically, 24 384-well standard polypropylene storage microplates 200 each housing 4 O-rings 2 per pin plate 100 can be sequentially labeled as plates #1-24. Each O-ring from the 24 storage plates 200 can be transferred to individual wells in 96 (#1-96) 384-well ELISA microplates. The top layer positioned O-rings ($1^{st}$ of 4 stacked O-rings 2 in each well 220), in each column# 1, of each of the 24 storage microplates 200 (384 top layered O-rings in column #1) can each be transferred to the $1^{st}$ column of wells 22 in the first set of 24 (#1-24) 384 well ELISA microplates 20. This process can be repeated with the $2^{nd}$ layer of O-rings 2 in each column #1 of each of the storage microplates 200, such that they are transferred into the $1^{st}$ column of wells in the second set of 24 (#25-48) ELISA microplates 20. The $3^{rd}$ layer of O-rings 2 in each column # 1 of each of the storage microplates 200 can then be transferred into the $1^{st}$ column of wells in the $3^{rd}$ set of 24 (#49-72) ELISA microplates 20. Likewise, the $4^{th}$ layer of O-rings 2 in each column # 1 of each storage microplates 200 can then be transferred into the $1^{st}$ column of wells in the $4^{th}$ set of 24 (#73-96) ELISA microplates 20. This process for column #1 can be repeated with column #2 of the #1-24 storage microplates 200 such that these O-rings 2 are sequentially transferred and rearranged in the same way to column 2 of the #1-96 ELISA microplates 20 Totally, 96 384-well ELISA microplates can be used rearrange all of the O-rings 2 from the 24 384-well storage microplates 200. Since the O-rings can be kept with ruminant sample fluids in the wells and the cold chamber, the common problems in the other planar slide or membrane microarray assays, such as dried up slides, inconsistent timing of process between samples and standard controls, etc., are eliminated in such a large scale of O-ring Array Assay.

More specifically, 24 384-well standard polypropylene storage microplates 200 each housing 4 O-rings 2 per well 220 can be sequentially labeled as plates #1-24. Each O-ring 2 from the 24 storage plates 200 can be transferred to individual wells in 96 (#1-96) 384-well ELBA microplates 20. For example, the first layer of 4 stacked O-rings 2 in each well 220 in each column 1 of all 24 storage microplates 200 (i.e. a total of 384 first layered O-rings 2 in column #1 wells) can be individually transferred to each well 22 in the $1^{st}$ 384 well ELBA microplate 20, such that each well 22 includes only one O-ring 2. Similarly, this process can be repeated with the $2^{nd}$ layer of O-rings 2 in each column 1 of the 24 storage microplates 200, such that they are each individually transferred into every well 22 of a $2^{nd}$ 384-well ELBA microplate 20, such that each well 22 includes only one O-ring 2. Likewise, the layer of O-rings 2 in each column 1 of the 24 storage microplates 200, can also be each individually transferred into every well 22 of a $3^{rd}$ 384-well ELISA microplate 20, such that each well 22 includes only one O-ring 2. Likewise, the $4^{th}$ layer of O-rings 2 in each column 1 of the 24 storage microplates 200, can also be each individually transferred into every well 22 of a $4^{th}$ 384-well ELIS A microplate 20, such that each well 22 includes only one O-ring 2. This process for column #1 of the storage plates 200 can be repeated with each column #2, and the remaining columns on the storage plate 200, for each of the 24 storage microplates 200 such that each layer of O-rings 2 in the same column are sequentially transferred and rearranged to wells 22 the same fresh 384-well ELISA microplate 20. Each column on the 24 storage plates 200 requires 4 384-well ELBA plates 20. Totally, 96 384-well ELISA microplates 20 can be used to rearrange all of the O-rings 2 from the 24 384-well storage microplates 200. Since the O-rings 2 can be kept with ruminant sample fluids in the wells and the cold chamber, the common problems in the other planar slide or membrane microarray assays, such as dried up slides, inconsistent timing of process between samples and standard controls, etc., are eliminated in such a large scale of O-ring Amy Assay.

FIG. 6 depicts a type of means for transferring and sorting O-rings 2. These means can be manual, automated, or a combination of both. A vacuum pump 28 can be in operable communication with a plurality of pipettes 36 configured to transfer and sort O-rings 2. Preferred means include a channel network 30 or ducts that connect the vacuum pump 28 to each pipette 36. More specifically, it is preferred that each pipette 36 includes multi-channel (e.g., 16 or 24 channels) permanent needles (e.g., made of metal, such as stainless steel) and a type of disposable (e.g., plastic, polypropylene) tip can also be used to cover and couple with each needle. Preferred tips can have a flat bottom with a thin opening of less than 0.2 mm, for example. This opening allows the vacuum pressure to freely pass through when the tip tightly covers a pipette needle that is in operable communication with the vacuum pump via the internal network of channels. This vacuum pressure through a thin opening 44 positioned at the bottom of tip allows the tip to hold a single O-ring firmly such that the researcher/operator can transfer the O-ring 2. In general, the O-rings 2 are typically transferred from a row of multi-layer O-ring affinity chromatograph columns, such as those positioned in a row of wells of a 384-deep-well storage microplate, to a row of wells in an ELISA microplate, or any other desirable location. More specifically, multiple pipettes 36 can be inserted in 16 wells on a column or 24 wells on a row of 384-deep-well standard microplate simultaneously in parallel.

The thin opening at bottom of a tip can be blocked by a single O-ring 2, positioned on top of a multi-layer O-ring affinity column, thus avoiding an individual pipette 36 picking up more than one O-ring 2 at a time during transfer. When the O-rings 2 are transferred into the designated wells of an ELISA microplate, or other desirable location, the vacuum pressure can be turned off allowing the O-rings 2 to be released into the wells, or other locations. According to certain embodiments, a variety of aspirators, with 8, 12, 16 and 24 channels of up to 60-millimeter long stainless needles, working in conjunction with a vacuum can be used for transferring multiple O-rings from a 96-deep-well or a 384-deep-well microplate. When a row of cylindrical tubes, in which there are a plurality of (e.g., over 100 layers) different capture-molecule coupled O-rings held in a tube rack of 96-deep-well or 384-deep-well microplate format, the aspirator with 8, 12, 16 and 24 channels of up to 60-millimeter long stainless needles can be used for O-ring 2 transferring. In some occasions, long arm and sharp forceps are also convenient for the O-ring transferring, one by one, such as when the sample size and biomarker multiplex are relatively small, for example.

FIG. 7 depicts an example of a disposable tip of a pipette 36. The disposable tip preferably includes a top opening configured to be coupled to the needle and the channel network 30 and a bottom opening 44 configured to 2 gently pick up one O-ring 2 per needle via suction pressure. Preferably the bottom opening 44 of the tip has a smaller diameter than the cross-section 24 length of an O-ring 2, such as 0.3 mm, or less, for example. Means for attaching and releasing the pipette tips can be configured to the means for sorting and/or transferring the O-rings 2. More specifically, these means can be configured to quickly attach or release all pipette tips at once, or individually. A plurality of the permanent multi-channel pipette needles can tightly be inserted into a row or column of disposable tips at the same time. A tip-releasing bar 32 can be positioned into a closed position along the surface of all pipette needles and the tips, thereby releasably securing the tips to the needles. When it is desirable to remove the tips, such as for attaching new tips, or when the transfer is finalized, the bar 32 can be positioned into a release position, such as by pushing down a tip-releasing button, and/or pressing down the tip-releasing bar, such that the tips will be released (e.g., pushed off from the needles, fall by gravity). Then, if desired, new tips can be loaded onto the needles and be used for the next transferring.

Controlling the amount of suction from the pump 28, can either increase or decrease pressure for picking up O-rings 2 or releasing them, respectively. A pistol switch 34 can be used to control the suction power and can be installed inside the pipette system. The pistol switch 34 is preferably positioned in the middle of the tubing connection between the vacuum pump 28 and pipettes 36 thereby allowing the flow of suction pressure, increase suction, decrease suction, or stop suction all together.

Preferably, the means for transferring and sorting O-rings 2 can include the same number of pipettes 36 as the number of pins, or wells, in a row or column, on a plate that the O-rings 2 are being transferred to or from. For example, a line of 16 or 24 pipettes can be used with a 384 well or pinned plate having 16 rows and 24 columns. Any desired amount of pipettes 36 can be used according to other embodiments, including the total number of pins or wells on a plate (e.g. 98 or 384 pipettes). More specifically, the suction generated from the pump 28 can suck an O-ring 2 from a well, pin, or other container, to the outside end 44 of the pipette 36. The O-ring 2 can then be transferred to another location, container, well, etc., depending on the specific experiment design. The means for transferring and/or sorting the O-rings 2 can be movable, preferably automated, such that it can suck an O-ring 2 from a particular position (e.g., well, pin, tubing container) and transfer it to another particular position (e.g., well, pin, container). The means can be configured to be continuously or integrally movable along a track, or guide, for example. Preferably, a pipette 36 only sucks one O-ring 2 per needle/tip at a time.

According to certain embodiments, there are one or more means for fluid disposal, which can be bottles, containers, or any suitable waste disposal means or device and commonly used in any biological lab in compliance with the appropriate biohazard disposal regulations and environmental protection laws. According to FIG. 6, a first and second bottle 38 and 40 are in operable communication (e.g., via tubing) with both the vacuum pump 28 and the pipettes 36. Waste fluid 42 is shown collected in the second bottle 40. According to certain embodiments, waste fluid 42 will be sucked up in addition to the one or more O-rings 2.

After being placed in their respective wells 22, the O-rings 2 coupled to their capture molecules 12 and their targeted biomarkers 14 can then be prepared for detection. Any suitable means for detection and methods known in the art can be used to quantify and/or qualify the capturing of biomarkers 14 to their O-rings 2. As each O-ring 2 rearranged in the same row(s) of wells in an ELISA microplate can be coupled to the same capture molecule 12, and thus the same biomarker 14, it is convenient to add only one type of detect molecule 16 (antibody) specific to the same capture molecule and biomarker complex. Preferably this is done using a manual or robotic, single or multi-channel pipette system, thus maintaining the specificity of detection as traditional sandwich ELISA does and avoiding the cross-contamination and non-specific complex interaction by other different detect molecules 16. This approach can be repeated exactly for the subsequent row(s) of wells housing different capture and biomarker complexes on the microplate 20 such that a total of 16 different detect molecules 16 or conjugates, are added respectively to 16 different capture and biomarker complex coupled O-rings in 16 rows of a 384-well ELISA microplate. It is possible for the first time in ELISA microarray to avoid using pre-mixed detect-molecules to probe a given capture-molecule and biomarker complex on supportive surface of solid substrates. Microplate rows can be substituted with columns, efficiently accommodating the O-ring array assay of various numbers of sample size and multiplexed biomarkers.

Once the O-rings 2 are rearranged in an ELISA microplate 20, any unbound biomarkers 14 or protein can be removed by a first round of washing with a detergent (e.g., Tween 20 at 0.05%) containing buffer one or more times in parallel, using a microplate washer, for example. Afterwards, detect molecules 16, such as a primary detect antibodies, selected to bind to a targeted captured biomarkers 14 can be added to the O-rings 2, thereby allowing the detect molecule 16 to form a dual-molecule sandwich complex with the targeted biomarker 14. According to advantageous embodiments, the detect molecules 16 can be coupled to biotin 17 or another suitable marker or reagent. A second round of washing can be carried out to remove the unbound detect molecule 16 from the O-rings 2. If the primary detect-molecule 16 is biotinylated, Streptavidin conjugated Alkaline Phosphatase (SCAP) can be added to and incubated with the O-rings 2 for about one hour in the same ELISA microplate 20, or other times sufficient to allow binding. An equal volume of alkaline phosphatase substrate solution can be added into each well 22 and incubated for a sufficient time to allow for binding with the streptavidin. Afterwards, a third round of washing can be carried out to remove the unbound streptavidin conjugated alkaline phosphatase.

Alternatively, if the primary detect-molecule is not conjugated to biotin 17, an AP-conjugated secondary detect-molecule (e.g., antibody) targeted against the primary detect-molecule can be added to the O-rings 2 in the microplate 20. Similarly, a fourth round of washing can be conducted to remove the unbound secondary detect-molecule.

Afterwards, an equal volume of Alkaline Phosphatase Substrate (such as 4-Methylumbelliferyl phosphate (4-MUP)) Solution can be added into the wells 22 of the microplate 20, allowing the AP hydrolyze AP substrate (4-MUP) into a fluorescent end product, methylumbelliferone. The concentration of fluorescent product (methylumbelliferone) in a homogeneous solution can be accurately and sensitively quantified utilizing a microplate spectrofluorometer. Any other suitable method of detecting whether a particular biomarker 14 has been captured by an O-ring 2 can also be used, with the teachings herein. This approach is advantageous as it is now possible for an ELISA microarray to quantify the fluorescent signaling in a homogeneous solution as a traditional sandwich ELISA does. Accordingly, in addition to the approach for achieving probing specificity using only one type of detect molecule for one biomarker (as opposed to mixing multiple detect molecules) as described in the previous section, the detection approach provided herein further maintains the sensitivity and reproducibility for multiplexed biomarker quantification.

The above methods and techniques for a DAS-ELISA O-ring Microarray Assay allow for the quantification and qualification of any number from 8 up to 384 biomarkers in a small volume (100 micro-L, undiluted biofluid) sample in parallel against that of seven 2-fold serial diluted standards of purified biomarker recombinants and one blank control. As a non-exclusive example, if a practitioner wanted to analyze 384 biomarkers in 8 small volume samples, they can first assemble a 384-layer O-ring affinity chromatograph columns in cylindrical containers (total 24 of them, for example). Then, they can easily set up the DAS-ELISA O-ring Microarray Assays as such that there are 16 different biomarkers assays for 8 samples, seven 2-fold serial diluted standards of purified biomarker recombinants (in duplicates) and one blank control (in duplicates) per a 384-well ELISA microplate, each of such assays taking one row of 24 wells and 384 different biomarkers assays utilizing a total 24 microplates. Such setup can also be easily adjusted for O-ring Microarrays for the quantification of 384 biomarkers in 32 small volume samples if needed. In preferred embodiments, there are 8 different biomarker assays for 32 samples, seven 2-fold serial diluted standards of purified biomarker recombinants (in duplicates) and one blank control (in duplicates) per a 384-well ELISA microplate. Each of such assays can take 2 rows of 48 wells in the same ELISA microplate, and there are 384 different biomarkers assays utilizing a total of 48 microplates.

In order to facilitate the unmet needs of basic and clinical research, DAS-ELISA-O-ring Arrays can be designed to quantitatively monitor the changes of up to 500 or more of the most active soluble biomarkers in human plasma. These biomarkers can be related to human disease, health, and environment interaction, and can non-exclusively include cytokines/chemokines, growth factors and receptors, for example. Because the industrial standard 384-well microplate is the commonly used ELISA microplate capable of housing the highest number of samples per basic unit, the teachings herein adapt the 384 microplate as a preferred, but non-exclusive, unit in designing, developing and validating the ELISA O-ring Array Assays with the capacity to quantify 384 biomarkers in multiple small volume samples. Any suitable well or other container can be used having a larger or smaller number of wells.

The methods herein can be used with any suitable DAS-ELISA kit currently available or available in the future. While there are currently approximately 254 validated DAS-ELISA kits (with 254 sets of capture antibody, biotinylated detect antibody, and purified biomarkers) available to accurately quantify biological markers in human biological fluids, the methods herein can be used with any suitable future kits for additional biomarkers as manufacturers continue to develop more DAS-ELISA kits for them.

According to certain embodiments, in addition to running DAS-ELISA O-ring assays for the 254 validated biomarkers format, a researcher could supplement the arrays with biomarkers of interest, such as 130 biomarkers for example. This could allow a research to accurately quantify the most active cytokines, chemokines and many other growth factors as well as their soluble receptors in human biological fluids, such as plasma and cerebrospinal fluids, for example. These biomarkers of interest can non-exclusively include a variety of cancer soluble markers (related to the cancer research), hormones (related to development, diabetes research), blood clotting factor (related to cardiovascular research), and the like, for example.

Single-Antibody-Capture ELISA O-Ring Array

Figure 2:
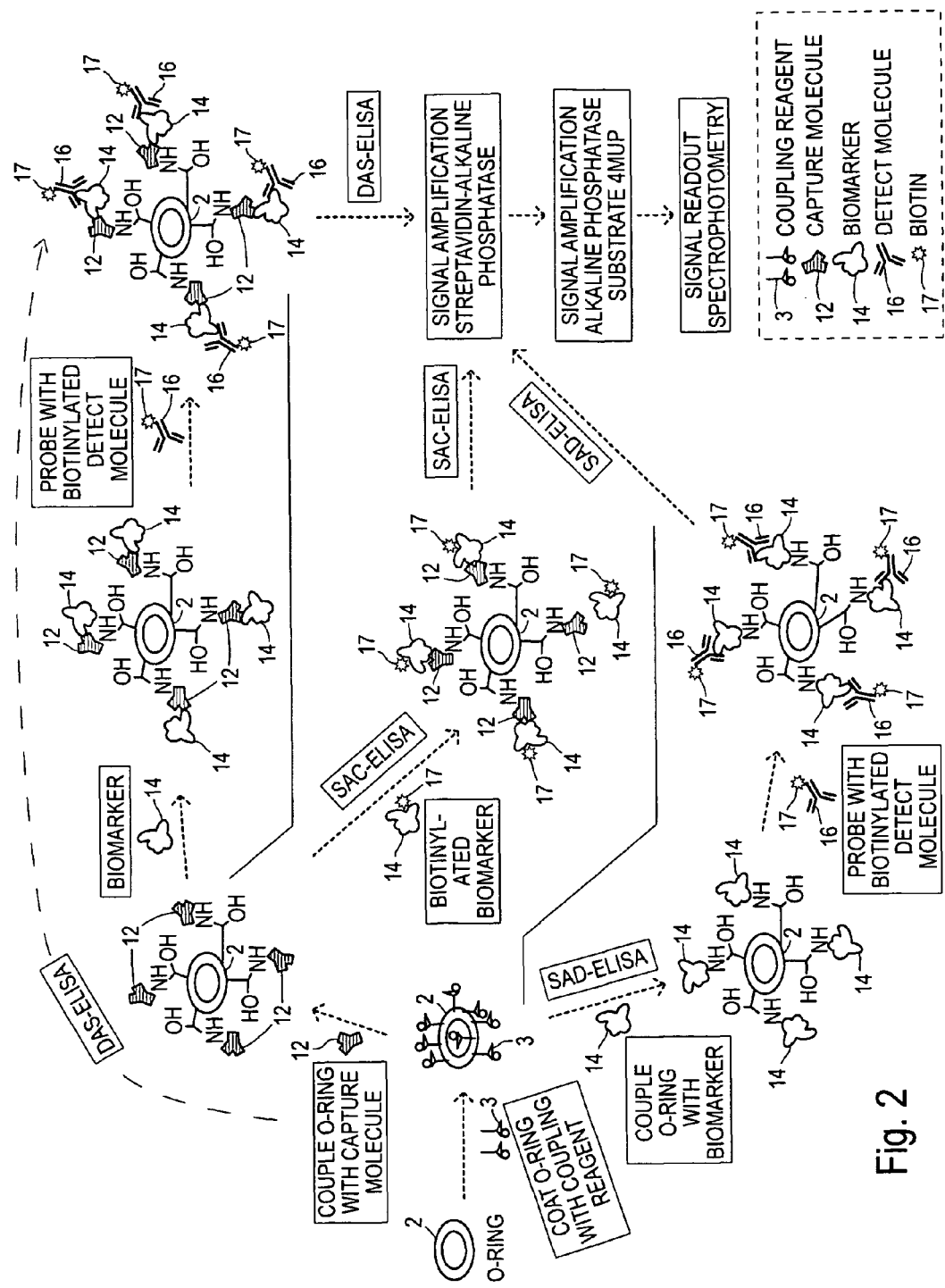
FIG. 2 depicts the use of O-rings in three different assays: DAS-ELISA, SAC-ELISA, and SAD-ELISA.

The term "Single-Antibody-Capture (SAC) ELISA O-ring Array," refers to an array of a predetermined number of solid uniformly shaped and sized, or substantially so, O-rings 2 each of which are individually coupled to a different capture molecule 12 (e.g., antibody) to bind a biomarker that is pre-labeled, or pre-conjugated, with biotin 17 (a preferred tag) or a fluorescent (not a preferred tag) in a sample. The general steps of a SAC ELISA O-ring Array are shown in FIG. 2. Similar to the DAS-ELISA O-ring Array, the solid uniform shape and size O-rings 2 are anchored through a pin, or a probe, in a pre-arranged sequential position and then packed into a deep well of microplate, or a tube to form a short or long multi-layer O-ring immuno-affinity chromatography column.

In contrast to DAS-ELISA O-ring arrays, while possible, it is difficult to set up standard controls for SAC-ELISA O-ring arrays. Accordingly, with respect to preferred embodiments, no standard controls are used for SAC-ELISA O-ring Arrays, provided herein. Similar to the DAS-ELISA O-ring arrays, preferred embodiments include placing O-rings 2 coupled with a the same specific capture molecule 12 in the same sequential position within each of the multi-layer O-ring immuno-affinity chromatography columns. Alternatively, O-rings 2 coupled to the same particular capture molecule 12 can be placed in different sequential positions within each of the multi-layer O-ring immuno-affinity chromatography columns, if the O-ring 2 is still trackable, for example. Each of the multi-layer O-ring immuno-affinity chromatography columns can be arranged to capture and isolate multiplex biomarkers 14, when fully exposed or incubated with a sample or standard fluid.

Similar to DAS-ELISA O-ring Arrays, one or up to hundreds of O-rings can also be placed into a multi-layer O-rings immuno-affinity chromatography column and be used for the quantification of an equivalent number of different biomarkers in a sample. In order to utilize SAC-ELISA O-ring Arrays to quantify multiplex biomarkers 14 in multiple samples, the number of identical, or substantially so, multi-layer immuno-affinity O-ring chromatography columns can equal the number of samples and their diluted samples respectively.

Unlike the DAS-ELISA O-ring arrays, SAC-ELISA O-ring arrays do not require a detect molecule (e.g., antibody) in the assay. On the contrary, a researcher can biotinylate, or otherwise mark, the biomarker (e.g., protein) 14 of each sample prior to capture by the O-rings 2. Preferably, an equal amount of total biotinylated biomarker (e.g., protein) 14 from each sample can be loaded into one of the identically set up, or substantially so, multi-layer immuno-affinity O-ring chromatography columns, thereby allowing the biomarkers 14 sufficient exposure to each of the capture molecule coupled O-rings 2 inside the chromatograph column. Afterward capturing, the O-rings 2 are sorted respectively from their multi-layer O-rings immuno-affinity chromatography columns and rearranged respectively into the wells 22 of a microplate 20, preferably the same ELISA microplate. This allows the O-rings with their captured biomarkers 14 from all groups of samples and their diluted samples to form a unique O-ring Array in a microplate. Thus, this unique O-ring Array in an ELISA microplate enables the simultaneous comparative quantification of a unique biomarker 14 in all groups of samples and their diluted samples. Based upon the prior design and plan of an experiment, a standard ELISA microplate (such as 384-well Microplate) can accommodate two or more unique O-ring Arrays for the quantification of one or more biomarkers in all groups of samples, and run simultaneously in parallel. One or up to hundreds of ELISA microplates 20 can be set up in a similar way to house one or hundreds of different O-ring arrays for the quantification of one or hundreds of corresponding targeted biomarkers 14 in all groups of samples.

According to alternative embodiments, when it is desirable to analyze a very large number of biomarkers (e.g., a number exceeding 384, such as up to 1536 biomarkers, or more). A plurality, such as, 4 or more different O-rings 2 can be anchored on each pin of a pin plate (e.g., 384 pin plate) respectively in a pre-arranged sequential order. A researcher can therefore anchor 1536 (4 O-rings×384 pins) different O-rings 2 on single plate, or more if desired. The equivalent amount of total biotinylated proteins from each sample can be dissolved in detergent containing buffer. The O-rings 2 anchored on the 384-pin microplate can incubate with the sample in different ways. According to one embodiment, a large volume of sample fluid (e.g., 10 mL) can be placed in a pool, and the O-rings 2 anchored on the pins can be dipped into the pool to sufficiently allowing binding of the biomarkers 14. This method can be used to detect extremely small concentrations of biomarkers 14, or scarcely present biomarkers 14. According to an alternative way of incubation, the O-rings 2 anchored on the pins can be individually dipped into wells on a microplate that contain sample fluid, such as 25-50 uL, for example. The number of wells should preferably match the number of pins on the plate. Similarly, based upon the size of samples and their diluted samples, a plurality of similarly arranged 384-pin microplates can set up to anchor the O-rings respectively for the same number of samples and their diluted samples during the incubation. This method can readily be adapted to use with Single-Antibody-Detect (SAD) ELISA O-ring Arrays, as well, as will be discussed below.

After incubating with the biotinylated biomarkers of each sample, each layer of O-rings that couple with the same capture molecule can be transferred respectively from the pin plates and placed respectively into the wells 22 of an ELISA microplate 20. Transferring the O-rings 2 with the same capture molecules 12 to the wells 22 of the same ELISA microplate 20, allows the O-rings 2 with the same captured biomarker 14, from all groups of samples and their diluted samples, to form a unique O-ring Array in a microplate. Depending on the goals of the particular experiment any desirable sorting and transferring of the O-ring 2 from a pin plate to a welled microplate can be used. According to preferred embodiments, one unique O-ring Array in an ELISA microplate can enable the comparative quantification of a unique biomarker in all groups of samples and their diluted samples. Based upon the prior design and plan of the particular experiment, one standard ELISA microplate (such as 384-well Microplate) can house two or more unique O-ring arrays for the quantification of one or more of biomarkers in all groups of samples run simultaneously in parallel. One or up to hundreds of ELISA microplates 20 can be set up in a similar way to house one to hundreds of different O-ring arrays for the quantification of one or hundreds of targeted biomarkers 14 in all groups of samples.

Similar to the DAS-ELISA O-ring Array, once the O-rings are placed in an ELISA microplate 20, the unbound sample proteins on the O-rings can be removed by a similar washing method. For example, a first round of washing can be done with a microplate washer and a detergent. After the first round of washing, the Streptavidin conjugated Alkaline Phosphatase can be added to and incubated with the O-rings in the wells 22 of a microplate 20. Afterwards, a second round of washing can be carried out to remove the unbound Streptavidin conjugated Alkaline Phosphatase.

Advantageously, an equal volume of Alkaline Phosphatase Substrate (such as 4-Methylumbelliferyl phosphate (4-MUP)) Solution can be added into the wells 22 of the microplate 20, thereby allowing the AP to hydrolyze the substrate (such as 4-MUP) into a fluorescent end product (such as methylumbelliferone). The concentration of fluorescent product (such as methylumbelliferone) in a homogeneous solution can be accurately and sensitively quantified using any suitable means or technology, including a microplate spectrofluorometer, for example.

Noticeably, since there are typically no standard controls used with the SAC-ELISA O-ring arrays herein, diluted controls from the same samples are used to estimate if the quantification of signaling is within the linear range of detection. The relative quantification can be calculated based upon the ratio of net signaling readout between two or more groups of samples. In preferred embodiments, the quantification of each biomarker between groups of multiple samples can be statistically analyzed when all of samples are similarly and simultaneously processed in parallel. Any suitable washing and detection means can be used as a substitute for the exemplary method above.

Single-Antibody-Detect (SAD) ELISA O-ring Arrays

The term "Single-Antibody-Detect (SAD) ELISA O-ring Array" refers the ELISA O-ring Arrays that couple the total sample biomarkers to the substrate of the O-ring Array surface and allow the detect molecule 16 to bind the specific biomarker 14. The general steps of this process are provided in FIG. 2. According to preferred embodiments, the SAD-ELISA O-ring Arrays herein enable the comparative quantification of multiplex biomarkers in a sample without using capture molecules (e.g., capture antibodies). For this method, an equal amount of total biomarkers from each sample, instead of capture molecules, can be covalently coupled to each of the O-rings. In general, SAD-ELISA O-ring Arrays are very similar to a reverse ELISA microarray, such that the biomarkers couple to the solid support substrate prior to being probed with a detect molecule 16.

According to preferred embodiments, SAD-ELISA O-ring Arrays can pack one or up to hundreds of the surface activated O-rings directly into short or long multi-layer O-rings immuno-affinity chromatography columns to allow the total number of biomarkers in a small volume sample (such as 100 uL) to covalently couple to the O-rings inside the column. In order to utilize SAD-ELISA O-ring Arrays to quantify multiplex biomarkers in multiple samples, an equivalent number of identically-made multi-layer immuno-affinity O-ring chromatography columns can be set up for each sample and their diluted controls respectively. Similar to SAC-ELISA O-ring Arrays, SAD-ELISA O-ring Arrays typically do not include the standard controls (with known concentration or amount of targeted biomarkers), because of the difficulty associated with the procedure. However, two or more groups of untreated controls, treated samples, and their diluted samples can be set up to allow comparative quantification of multiplex biomarkers between groups.

After coupling with the known amount of biomarkers 14 of each sample, one or more biomarker coupled O-rings from each sample (from all groups, undiluted and diluted samples) can be placed in the same ELISA microplate 20 to form a unique O-ring Array. The O-ring Array can thus be set to be probed by one unique detect molecule 16, such as a detect antibody, whether conjugated with biotin, another marker, or not. According to certain embodiments, an O-ring Array ELISA microplate is configured to allow the comparative quantification of a unique biomarker 14 that is present in groups of samples and their diluted samples. Based upon the design of the experiment, a standard ELISA microplate (such as 384-well microplate) can house two or more unique O-ring Arrays for the quantification of two or more of biomarkers in all groups of samples run simultaneously in parallel. One or up to hundreds of ELISA microplates can be set up in a similar way to house one or hundreds of different O-ring arrays for the comparative quantification of one or hundreds of targeted biomarkers 14 present in all groups of samples. As there are typically no standard controls included in SAD-ELISA O-ring Arrays, the diluted controls from the same samples can be used to estimate if the quantification of signaling is within the linear range of detection. Each sample can be diluted into two or three separate samples respectively (depending upon the diluting factors such as by 10, or 100, or 1000 fold).

According to the teachings herein, and similar to the embodiments described above, a first round of washing can to remove the un-coupled proteins from the O-rings 2 after they are sorted and rearranged into the wells of ELISA microplate using a microplate washer and detergent, for example. Additionally, a non-specific-protein blocking buffer (such as 4% of casein or bovine serum albumin) can be added to wells holding an O-ring 2 and incubated for a sufficient time, in order to prevent the non-specific binding of a detect molecule to the O-ring and the microplate as well. The blocking buffer can be removed with the second round of washing. Afterwards, a specific detect molecule can be added to the SAD-ELISA O-ring array, thereby simultaneously probing targeted biomarkers on all O-rings, representing all groups of samples, in parallel. After the detect molecule incubates with the targeted 0 ring array for the sufficient time, the third round of washing procedure can be performed to remove un-bound detect molecules.

The next sequential procedure is to quantify the detect molecules 16 bound to the specific biomarker 14 coupled to the surface of O-rings 2. Any suitable methods of quantifying the detect molecules 16 can be used herein, such as the following examples. A researcher could biotinylate all detect molecules so that the Streptavidin-conjugated-Alkaline Phosphatase can be used to probe and form the complexes comprising of specific biomarker, detect molecule, and Streptavidin-conjugated-Alkaline Phosphatase. Another non-exclusive way to quantify the detect molecules is to use non-biotinylated primary detect molecules to probe or bind the specific biomarker first and then use Alkaline Phosphatase-conjugated secondary detect molecules to probe or bind to the primary detect-antibodies. In both of these steps, Alkaline Phosphatase can be used for signaling amplification to generate a fluorescent product in each well of ELISA microplate. These two approaches are common examples but are expressly non-limiting. Detect molecules against specific biomarkers are readily available in the form of AP or HRP conjugated status and can be used for both the probing and the signal amplification purposes.

The SAD-ELISA O-ring Arrays herein can provide flexibility for selecting either one or both of two signaling amplification methods. In addition, the primary detect molecules (e.g., antibodies) used for these methods can be chosen from a variety of commercial and proprietary sources. More specifically they can be derived from several different species, such as rabbit, mouse, rat, horse, donkey, sheep and goat, and come in biotinylated form or non-biotinylated form, purified form or in a mixture with carrier protein, or the un-purified form in serum, or in ascite, and the like, for example.

The comparative quantification can be calculated based upon the difference in ratio of net fluorescent signaling output between two or more groups of samples using spectrometry.

Since there are typically no standard controls included in SAD-ELISA O-ring Arrays, diluted samples can be used as a corresponding reference to estimate if the quantification of fluorescent signaling is within the linear range of detection. The quantification of each biomarker between groups of multiple samples can be statistically analyzed when all of samples are similarly and simultaneously processed in parallel. In comparison, the SAD-ELISA O-ring Arrays use much less capture molecules (e.g., antibodies) than the SAC-ELISA O-ring Array.

The scale and arrangement the O-ring microarrays disclosed herein can be flexibly adapted to include low, mid, and high level multiplexing biomarker quantification in various sizes of available sample, including one or more small, medium, and large volume samples. Additionally, the size of the O-rings can also be flexible depending on their particular use. For certain embodiments, two different types of O-ring sizes can be used depending on the microplate and the size of the well. More specifically, one size of O-ring can be used in a standard 384 well microplate and another size of O-ring can be used in a standard 96 well microplate, likewise different sized O-rings could be used for deep well microplates.

After the initial procedure of biomarker capturing, those O-rings are sorted and replaced into 384 well microplate one by one using the single-O-ring transferring tool or specially designed multiple-O-ring transferring pipette according to the pre-arrangement format. Such a pre-arranged format is designed to ensures that the O-rings capturing the same biomarkers from all of multiple samples and their diluted controls are replaced in the same 384 well microplate and simultaneously processed in parallel during the sequential procedures of washing, probing and signal quantification as described above.

Not only two pre-arrangement formats presented here, but a variety of other similar formats can be adapted according to the multiplexing level of biomarkers and the size of sample population. In addition to using the O-ring Container provided herein, there are other ways for contacting the O-rings and their capture molecules to a sample.

WORKING EXAMPLE

Example 1

The Quantitative Profiling of 32 Cytokines/chemokines Released from Human Peripheral Blood Mononuclear Cells In Vitro Materials and Instruments O-rings for Array: The O-rings were made of a fluoroelsatomer polymer and had a 1.5-mm internal diameter and a 1 mm cross-section.

Organosilicone Coupling Reagent: 3-glycidoxypropyltrimethoxysilane (catalogue #440167, Sigma-Aldrich)

Microplates for Array: 384-deep-well polypropylene standard microplates, 384-well polystyrene spectrometer assay microplates, and a 384-well microplate sealing mat, all were purchased from Phenix Research Products, Inc.

Dual Antibodies Pairs for Sandwich ELISA: As Table#1 depicts a total of 254 dual antibodies pairs for Sandwich ELISA for accurately measuring 254 specific cytokines/chemokines, growth factors and their soluble receptors in R&D Systems, Inc. (614 McKinley Place NE, Minneapolis, Minn. 55413, USA). The 32 biomarkers shown in Table # 2 below were tested herein. Each of the dual antibody pairs include a capture-antibody and a biotinylated detect-antibody. The standard controls of cytokines/chemokines, growth factors and their soluble receptors were the recombinant protein of high purity.

ELISA Signaling Detection and Amplification: Streptavidin-conjugated with Alkaline Phosphatase was purchased from GE Life Bioscience. 4-Methylumbelliferyl phosphate (4-MUP) was used as the substrate for alkaline Phosphatase and was ready to use in buffer solution from Sigma (Catalogue# M3168). The fluorescent end product, methylumbelliferone, was measured with excitation at 360 nm and emission at 440 nm.

Microplate Washer: Microplate washer ELx405, made by HT BioTek Instruments, Inc (100 Tigan Street, Winooski, Vt. 05404). The 384 well microplate washer utilizes 192 pairs of aspiration and dispense-tubes to provide rapid and effective aspiration and dispensing of fluid. This washer uses the dual-action manifold design and allowed independent control, both vertically and horizontally, of the aspiration and the dispense manifolds. There was no adjustment for this type of microplate washer to wash the O-rings in 384-well ELISA microplate. When a single O-ring was placed in a well of 384-well ELISA microplates, the washer worked normally for the aspiration and the dispensing without damaging the O-rings inside the wells.

Microplate Spectrofluorometer: This instrument was made by Molecular Devices (1311 Orleans Drive, Sunnyvale, Calif. 94089). Because a single microplate often presented a range of fluorescence intensities greater than three orders of magnitude, this spectrofluorometer had an advantageous function to avoid saturating the photomultiplier tube. The signal was also calibrated against an internal standard, so the reported relative fluorescent unit (RFU) values of individual samples could be accurately compared. There was no need to adjust the Microplate Spectrofluorometer for reading the signal in each well of 384-well ELISA microplate with O-rings laying flat on the bottom of wells.

Procedure

Preparation of Organosilicone Coupling Mixture: 3 parts 3-glycidoxypropyl-trimethoxysilane (catalogue #440167, Sigma-Aldrich), 96 parts 95% ethanol, and 1 part of glacial acetic acid was freshly mixed at room temperature.

Covalently Coating of Organosilicone Coupling Reagent to O-ring Arrays: The O-rings were submerged and incubated in the organosilicone coupling solution over night at room temperature. Afterwards, the O-rings were rinsed with 95% ethanol three times and completely desiccated in a vacuum chamber at room temperature. The O-rings were then further cured at 65° C. over night and packed in the vacuum-sealed container until use.

Covalently Coupling Antibodies to O-ring Arrays: After being pre-coupled with Organosilicone coupling reagent as described as in the above procedure, each of the O-rings was incubated with a specific capture antibody dissolved at 5 ug/milli-L in solution of 0.1 M sodium carbonate, pH 9.3, over night to allow coupling. Afterwards, the O-rings were rinsed with PBS once, and submerged with 4% of casein in PBS for two hours at room temperature which allowed the casein protein to block the non-specific binding sites on the surface of O-rings. The O-rings were desiccated in a vacuum environment over night. The O-rings and their coupled capture-antibodies were then packaged in vacuum-sealed plastic bags and stored at 4° C. until use.

Assembling of Multi-Layer O-rings Affinity Chromatography Column in 384-deep-well Microplate: 32 dual antibodies pairs for Sandwich ELISA were chosen for measuring 32 specific cytokines/chemokines, growth factors and their soluble receptors and were obtained from R&D Systems, Inc.

(614 McKinley Place NE, Minneapolis, Minn. 55413, USA) (seen Table#1). These 32 biomarkers are provided in Table 2 below. Each of the capture-antibodies was respectively coupled to 46 O-rings as described above in the procedure for covalently coupling antibodies to O-ring arrays. 46 identical sets of 32-layer O-ring affinity chromatography columns were separately placed into 46 wells on two rows of one 384-deep-well polypropylene standard microplate respectively for 30 samples (5 media samples from three groups: two different treatment groups and one group of un-treatment control, total 15 media samples in duplicate wells) and 16 standard controls (seven 2-fold serial-dilution standard controls of 32 purified biomarker recombinant proteins and one blank control (Bovine Serum Albumin), each in duplicate wells.) Within each of the 46 identical chromatography columns, 32 different coupled sets of capture-antibodies and O-rings were sequentially stacked and formed into a 32-layer O-ring affinity chromatography column in each well of a 384-deep-well polypropylene storage microplate. This setup was configured to capture 32 specific biomarkers from these 30 media samples and 16 standard and blank controls as described above.

Figure 8:
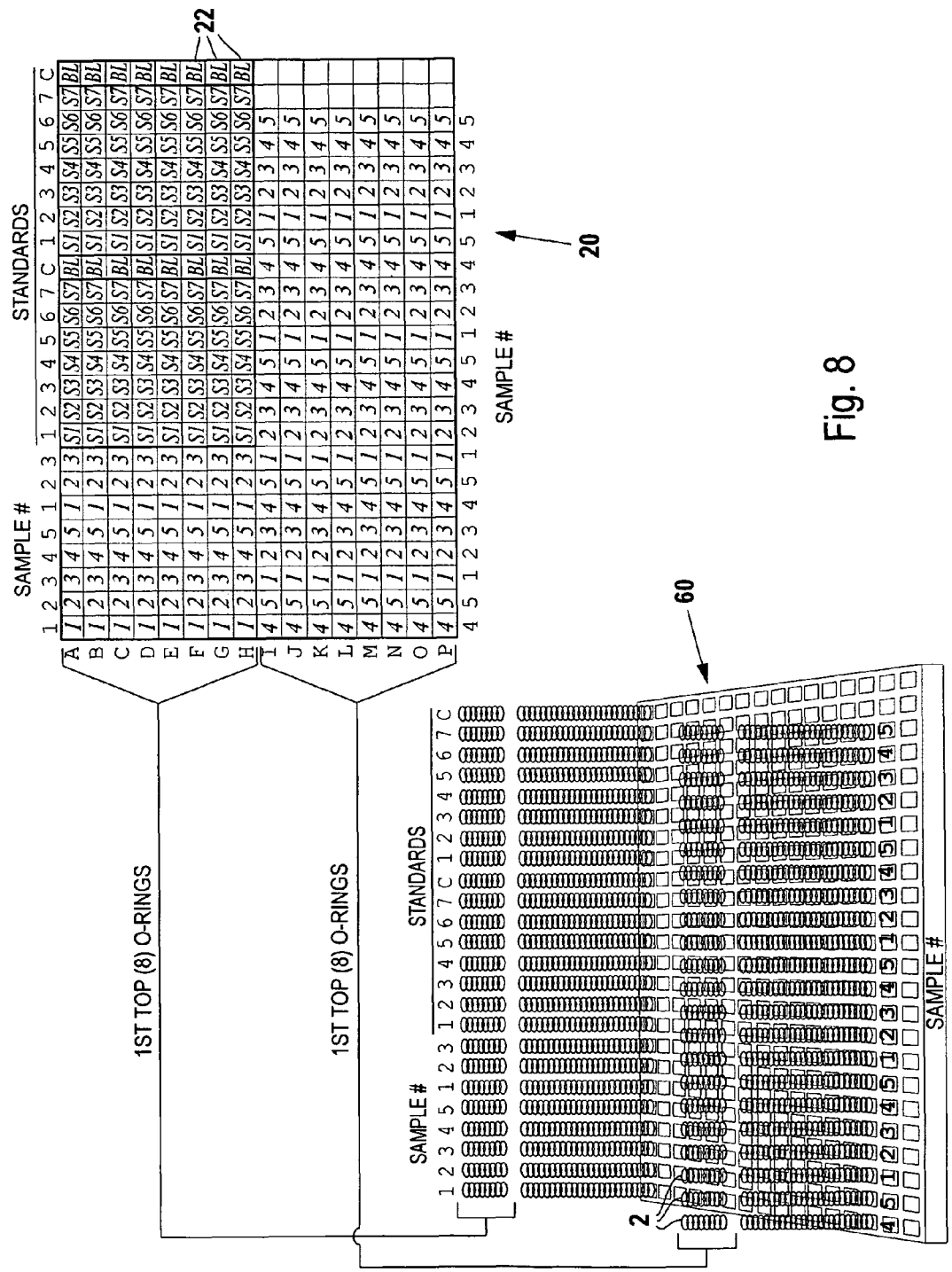
FIG. 8 depicts the organization and transfer of 46 columns of 32 different O-rings from a 384 deep well storage plate to four different 384 well ELISA microplates.

FIG. 8 depicts this set up in detail. The storage microplate 60 housed two rows of chromatography columns, 24 wells of columns in the top row and 22 wells of columns in the bottom row.

Preparation of Human Peripheral Blood Mononuclear Cells (PBMCs): 10 milli-L of blood were drawn by Venipuncture, anticoagulated with ethylenediaminetetraacetate (EDTA), and collected into 4 milli-L of endotoxin-free tubes (Vacutainer, Becton-Dickinson, NJ, USA) in the morning. Within 1 hour of collection, isolation of peripheral blood mononuclear cells (PBMCs) was carried out using Ficoll-Plaque gradient method (Boyum, 1974). PBMCs were enriched at 10-E6/milli-L during isolation and re-suspended in RPMI 1640 medium supplemented with 10% fetal calf serum, 4 mM L-glutamine, 25 mM Hepes buffer, 50 U/milli-L penicillin, and 50 ug/milli-L streptomycin.

Preparation of Abetal-42 oligomer (O-Ab42): The synthetic human peptide Abeta 1-42 was dissolved and incubated in phosphate-buffered saline (PBS) (1 mg/milli-L) for 7 days at 37° C.

Induction of Cytokines/Chemokines Release from PBMCs by Abetal-42 oligomer and bacterial lipopolysaccharide in vitro: The isolated PBMCs were plated and incubated overnight at 37° C. in a 95% humidified, 5% CO2 cell culture incubator, with equal volume (500 micro-L) of blank RPMI-1640 media, a mitogenic stimuli bacterial lipopolysaccharide (LPS) at 1 ng/milli-L in RPMI-1640 media and a mixture of Abetal-42 peptide oligomer in RPMI-1640 at 100 ng/milli-L. Each treatment was repeated in five separate wells of 24-well cell culture microplate. A total of 15 wells of cultured PBMCs were set up. The equal volume (400 micro-L) of incubation culture media was collected into the fresh 1.5 milli-L eppendorf centrifuge tube from each of treated sample culture well and then spun at 2000 rpm in microcentrifuge for 15 minutes at 4° C. The equal volume (300 micro-L) of media supernatant was transferred to the second fresh eppendorf tube and stored at −70° C. until assay.

Preparation of Culture Media Samples: Each of the 15 media supernatant samples was diluted with the sample diluting buffer containing 0.1% Tween-20 and 4% bovine serum albumin in Tris buffer saline (TBS, Tris-Chloride 20 mM, Sodium Chloride 150 mM, pH 7.5) by 2 fold.

Dual Antibody Sandwich ELISA O-ring Microarray Assay for Quantification of 32 Biomarkers In PBMCs Culture Media Samples: Each of the 15 media samples was loaded into two separate wells, each housing a sing multi-layer o-ring affinity chromatography column, in a 384-deep-well microplate 60, which was assembled as shown in FIG. 8. 32 purified biomarker recombinant proteins obtained from commercial sources were mixed into one stock solution of standard controls with known final concentration of each biomarker in the sample diluting buffer containing 0.1% Tween-20 and 4% bovine serum albumin in TBS, (Tris-Chloride 20 mM, Sodium Chloride 150 mM, pH 7.5). The stock solution of standard control mixture was consequentially diluted by serial 2-fold into seven concentrations from the highest concentration to the lowest concentration (Standards 1-7), as recommended by manufacturer. Each of diluted standard controls was also loaded in two separate wells housing a single multi-layer O-ring Affinity chromatography columns in a 384-deep-well microplate 60. The two blank controls (Standard C shown in FIG. 8) for each biomarker quantification were the sample diluting buffer only and loaded in two separate wells, each housing a single multi-layer O-ring Affinity chromatography column. All of the media samples, standard controls and blank control were loaded at 100 micro-L per well respectively. After loading the samples and controls, an O-ring fixture probe (T-shape, 32 mm length×0.76 mm Outer diameter) was placed through the apertures of the O-rings organized in a stacked column form in each well. A 384 well microplate sealing mat was used to air-tightly seal all of microplate wells.

As result, there were 30 wells of PBMCs culture media samples, 14 wells of standard controls and 2 wells of blank controls, total 46 individual wells. Then, those 46 wells were incubated on a vertical-rotator at 5 rpm for 16 hours at 4° C. of temperature, allowing the media samples and controls to fully expose to 32 O-rings respectively in their own wells. Meanwhile, four 384-well polystyrene ELISA microplates were loaded and incubated with 100 micro-L of blocking buffer containing the 4% bovine serum albumin in TBS (Tris-Chloride 20 mM, Sodium Chloride 150 mM, pH 7.5) in each well, allowing the bovine serum albumin protein to saturate the non-specific protein binding sites on the surface of polystyrene microplate wells for at least 4 hours at room temperature.

After incubating with media samples and standard controls, each of the 32 O-rings in each of the 46 deep wells of 384-well storage microplate 60 was taken out and rearranged into the wells of 384-well ELISA microplates 20, with 1 O-ring 2 per well 22. The wells 22 of 384-well ELISA microplate 20 were pre-blocked with 4% bovine serum albumin in TBS buffer. Thus, every set of 46 O-rings with the same capture antibody/biomarker complex (O-rings from all samples, standards and blank controls) were taken out of their 46 deep wells on a 384-well storage microplate, and individually rearranged in fresh 46 wells (1 O-ring per well) in two rows of a 384-well ELISA microplate 20, using forceps. Of the 46 O-rings, 24 O-rings were taken from the top row of deep wells and 22 O-rings were taken from the bottom row of deep wells. More specifically, given a column of 32 O-rings in one deep well, 8 O-rings would be taken out sequentially one by one and transferred to 8 individual wells 22 on the corresponding column of ELISA microplate 20.

368 O-rings from 8 different sets of 46 O-rings were transferred separately into 368 wells on a 384-well ELISA microplate 20. Totally, 32 different sets of 46 O-rings (1472 O-rings) were transferred to four 384-well ELISA microplates 20. Each set of 46 O-rings was sequentially replaced in the same two rows of wells in each of the 384-well ELISA microplates. Details of the rearrangement of the O-rings in one of the four 384-well ELISA microplates 20 are illustrated in FIG. 8. Such a rearrangement enabled each set of 46 O-rings (from all samples, standard and blank controls) with the same biomarker/capture-antibody complex to be probed and quantified in the same ELISA microplates in the sequential procedures.

The O-rings in four 384-well ELISA microplates were washed three times with TBS washing buffer containing 0.05% Tween 20 on Microplate washer ELx405 (see the section of Materials and Instruments). Basically, the Microplate washer ELx405 dispensed 140 micro-L of TBS-washing buffer into each well of ELISA microplate and allowed the O-ring soak in the washing buffer for a few seconds. The Microplate Washer ELx450 completely aspirated the washing buffer from all wells of ELISA microplates. The cycle of dispensing and aspirating was repeated three times by Microplate Washer ELx450 with a computer-assisted program. This washing procedure was to remove the unbound media samples or standard controls from their respective O-rings in wells of ELISA microplate.

32 detect antibodies were separately diluted in sample diluting buffer (4% bovine serum albumin in TBS buffer) according to the instruction of ELISA kit Manufacturer R&D Systems, Inc. 50 micro-L of each detect antibody was added respectively onto their corresponding O-rings with the targeted specific biomarker/capture antibody complexes in the wells of ELISA microplates 20. After adding the detect antibodies, the ELISA microplates 20 were briefly spun for 1 minute at 300 rpm in a standard microplate centrifuge. A visual inspection was made to see that each O-ring was squarely laying flat on the bottom of well of ELISA microplates 20. Then, the detect antibodies were incubated with each O-ring in the ELISA microplates for at least 2 hours at room temperature and on the horizontally Orbit shaker rotating at 60 rpm. After incubating with detect antibodies, the O-rings in the ELISA microplates 20 were washed three times with the washing buffer to remove the unbound detect antibodies by Microplate Washer ELx450 with the same computer-assisted program as used in the previous washing procedure.

Streptavidin-conjugated Alkaline Phosphatase (AP) was diluted in sample diluting buffer (4% bovine serum albumin in TBS buffer) at volume ratio 1:10k, AP: Buffer. 50 micro-L of AP solution was added respectively onto all O-rings in the wells of ELISA microplates. After adding the AP solution, the ELISA microplates were also briefly spun for 1 minute at 300 rpm in a standard microplate centrifuge. The visual inspection was also needed to make sure that each O-ring was squarely laying flat on the bottom of well of ELISA microplates. Then, the AP solution was incubated with the each O-ring in ELISA microplates for at least 2 hours at room temperature and on the horizontally Orbit shaker rotating at 60 rpm. After incubating with AP solution, the O-rings in ELISA microplates were washed three times with the washing buffer to remove the AP solution by Microplate Washer ELx450 with the same computer-assisted program as used in the previous two washing procedure.

4-Methylumbelliferyl phosphate (4-MUP) buffer solution from Sigma (Catalogue # M3168) was added to all wells containing O-rings with 100 micro-L/well and incubated for at least 30 minutes at room temperature. The fluorescent end product by AP, methylumbelliferone, was read by a microplate spectrofluorometer at excitation 360 nm and emission 440 nm. The Relative Fluorescent Units (RFUs) of a serial dilution of each purified specific biomarker (standard control) were respectively interpolated into a standard curve. A total of 32 standard curves were drawn by computer software. The concentration of the 32 biomarkers in 15 media samples (each sample was independently quantified twice in O-ring Array Assays) was calculated based upon the RFUs of each sample's well against those 32 standard curves of RFUs.

Data Analysis, Result and Conclusion: The lower limit and the linear range of detection for each Dual-Antibody Sandwich ELISA O-ring Array Assays were the same as those of traditional and individual ELISAs as R&D Systems, manufacturer of ELISA kits, provided in the corresponding ELISA data sheet. Noticeably, within the linear range of detection, the duplicates of samples and standard control demonstrate a very close result from two independent O-rings. As seen in Table #2, below, data analysis demonstrated that the average coefficient of variation (CV) of quantification for all of the 32 biomarkers in all of samples was about 5-8%. Since the whole procedure of Dual-Antibody Sandwich ELISA O-ring Microarray Assay works well for the quantification of 32 biomarkers in 15 individual media samples, a variety of O-ring Microarray Assay Examples are also proposed (See Example 2-4) but not limited only to those Examples.

TABLE 2

Abeta-42 or Lipopolysaccharide induced increase or decrease of 32 cytokines/chemokines release from human peripheral blood mononuclear cells in vitro.

| | | Abeta 1-42 oligomer Treatment (n = 5) | | | Lipopolysaccharide Treatment (n = 5) | | |
|---|---|---|---|---|---|---|---|
| | | Biomarker Level Above or Below Negative Control (in Fold, N = 5 ) | | | | | |
| | | Average | SD | CV | Average | SD | CV |
| 1 | ENA-78 (CXCL5) | 7.085 | 0.124 | 1.7% | 9.839 | 0.409 | 4.2% |
| 2 | G-CSF | −4.621 | 0.171 | 3.7% | 10.302 | 0.267 | 2.6% |
| 3 | GM-CSF | 1.002 | 0.021 | 2.1% | 13.397 | 0.464 | 3.5% |
| 4 | GRO-alpha (CXCL1) | 2.002 | 0.048 | 2.4% | 2.975 | 0.115 | 3.9% |
| 5 | IFN-gamma | 2.340 | 0.039 | 1.7% | 4.556 | 0.066 | 1.4% |
| 6 | IL-1alpha | −2.196 | 0.072 | 3.3% | 15.765 | 0.451 | 2.9% |
| 7 | IL-1beta | 20.231 | 4.385 | 21.7% | 20.865 | 0.957 | 4.6% |
| 8 | IL-1RA | 2.857 | 0.128 | 4.5% | 3.094 | 0.529 | 17.1% |
| 9 | IL-2 | 2.445 | 0.063 | 2.6% | 10.537 | 0.506 | 4.8% |
| 10 | IL-3 | −11.525 | 1.292 | 11.2% | −16.379 | 3.361 | 20.5% |
| 11 | IL-4 | −2.342 | 0.085 | 3.6% | 2.258 | 0.055 | 2.4% |
| 12 | IL-5 | −8.691 | 2.725 | 31.3% | 42.207 | 1.123 | 2.7% |
| 13 | IL-6 | −2.274 | 0.116 | 5.1% | 4.948 | 0.160 | 3.2% |
| 14 | IL-6R | 10.505 | 0.392 | 3.7% | 13.788 | 0.216 | 1.6% |
| 15 | IL-7 | −8.498 | 1.194 | 14.1% | 3.449 | 0.066 | 1.9% |

TABLE 2-continued

Abeta-42 or Lipopolysaccharide induced increase or decrease of 32 cytokines/chemokines release from human peripheral blood mononuclear cells in vitro.

|  | Abeta 1-42 oligomer Treatment (n = 5) | | | Lipopolysaccharide Treatment (n = 5) | | |
|---|---|---|---|---|---|---|
|  | Biomarker Level Above or Below Negative Control (in Fold, N = 5 ) | | | | | |
|  | Average | SD | CV | Average | SD | CV |
| 16 IL-8 (CXCL8) | 16.321 | 0.427 | 2.6% | 23.463 | 0.609 | 2.6% |
| 17 IL-10 | −1.062 | 0.019 | 1.8% | 12.703 | 0.470 | 3.7% |
| 18 IL-11 | −7.232 | 0.899 | 12.4% | −10.105 | 2.106 | 20.8% |
| 19 IL-12p40 | 17.356 | 0.506 | 2.9% | 24.315 | 0.504 | 2.1% |
| 20 IL-12p70 | 1.992 | 0.031 | 1.5% | 1.010 | 0.016 | 1.5% |
| 21 IL-13 | 2.050 | 0.032 | 1.6% | 15.917 | 0.187 | 1.2% |
| 22 MCP-1 (CCL2) | 12.484 | 2.142 | 17.2% | 16.540 | 0.428 | 2.6% |
| 23 MCP-2 (CCL8) | 18.260 | 3.538 | 19.4% | 18.211 | 0.486 | 2.7% |
| 24 MCP-3 (CCL7) | 16.681 | 3.538 | 21.2% | 10.055 | 0.182 | 1.8% |
| 25 MIP-1alpha (CCL3) | 1.379 | 0.189 | 13.7% | 15.504 | 0.384 | 2.5% |
| 26 MIP-1beta (CCL4) | 4.747 | 0.410 | 8.6% | 7.227 | 0.284 | 3.9% |
| 27 RANTES (CCL5) | 3.106 | 0.068 | 2.2% | 4.444 | 0.097 | 2.2% |
| 28 sTNF-R1 | 5.418 | 0.465 | 8.6% | 4.539 | 0.099 | 2.2% |
| 29 sTNF-R2 | 3.476 | 0.215 | 6.2% | 4.116 | 0.105 | 2.6% |
| 30 TGF-alpha | −4.539 | 0.183 | 4.0% | −4.527 | 0.202 | 4.5% |
| 31 TGF-beta1 | −4.743 | 0.210 | 4.4% | −4.766 | 0.046 | 1.0% |
| 32 TNF-alpha | 3.801 | 0.197 | 5.2% | 13.721 | 0.149 | 1.1% |
| Average CV |  |  | 7.7% |  |  | 4.2% |

Prophetic Examples

Example 2

The Quantitative Profiling of 32 Cytokine/chemokine Biomarkers in Hundreds of Biofluid Samples The materials and instruments are the same as are used in Example 1. The procedure of DAS-ELISA O-ring array assay is can adapt to the hundreds of samples for the same 32 biomarkers quantification. Briefly, the adjustments are highlighted as follow. 32 different capture-antibodies coupled O-rings are packed identically in each well of 384 deep well storage microplate, thus forming 32 layers affinity chromatography column in each well; up to 368 individual small volume sample fluids and 7 serial 2-fold diluted 32-biomarkers mixture standard controls and 1 blank control in duplicate are loaded respectively into the wells of a 384 deep well microplate. Each layer of rings can be sequentially taken out from 32-layers of O-rings in each deep well of storage microplate and rearranged respectively into the corresponding well of 32 separate ELISA microplates. This can be done using an automated pipette system as shown in FIG. 6, or manually using forceps, pipettes, or probes, for example. 32 ELISA microplates respectively house 32 different specific O-ring Arrays, each of which the O-ring Arrays capture only one specific biomarker during the fluid samples and standard controls incubation.

Example 3

Single-Antibody-Capture-ELISA O-ring-Arrays in two 384 well Microplates for Comparative Quantification of 32 Biomarkers in 21 Small Volume Samples This example is used to demonstrate the procedures of Single Antibody Capture-ELISA O-ring Arrays. The instruments are the same as are used in Example 1, but the capture antibodies in the section of materials are used in this example and can be changed as the researcher desires. There are no detect-antibodies for the SAC-ELISA O-ring Array Assay in this example. 32 different capture antibodies coupled O-rings are packed in each of 24 wells at the first row of a 384 deep well storage microplate to form a Multi-layer O-ring Affinity Chromatography Columns. The known amount of biotinylated total proteins from 21 samples (7 samples in three different treated groups) and 3 non-biotinylated blocking protein controls (C) are respectively loaded into a column and incubated with 32 O-rings for more than 16 hours at 4° C. and on vertical rotator at 10 rpm after the air-tight sealing with a 384-well seal mat. 32 biomarker-capture O-rings from each Multi-layer O-ring Affinity Chromatography Columns are respectively rearranged into two 384 well ELISA microplates and are probed with Streptavidin-conjugated Alkaline Phosphatase simultaneously in parallel for comparative quantification of 32 biomarkers in 21 samples.

Example 4

Single-Antibody-Detect-ELISA O-ring Arrays in two 384 Well Microplates for the Comparative Quantification of 32 Biomarkers in 21 Small Volume Samples This example is used to demonstrate the principles and procedures of Single Antibody Detect-ELISA O-ring Arrays. The instruments are the same as are used in Example 1. The detect antibodies used for this example can be whatever the researcher desires. There are no the capture-antibodies for the SAD-ELISA O-ring Array Assay in this example. The identical 32 of 3-glycidoxypropyltrimethoxysilane coupled O-rings are assembled in each of 24 Wells at the first row of 384-Deep-Well Microplate. The known amount of total proteins from 21 samples (7 samples in three different treated groups) and 3 blocking protein controls (C) are respectively loaded into above 24 Wells at the first row of 384-Deep-Well Microplate and incubated with 32 O-rings in each well for over 16 hours at 4° C. and on vertical rotator at 10 rpm after the air-tight sealing with 384-well seal mat. 32 O-rings from each of 24 Wells of 384-Deep-Well Microplate are respectively rearranged into two 384 well ELISA microplates. 32 different biotinylated detect antibodies are prepared in 32 channel reagent wells in two 16 channel well plates and added to the sample proteins coupled O-rings in two 384 well ELISA microplates. It is understood by those of skilled in the art that the steps in the above method can be practiced in various different orders. The listing of the steps in the particular order described above does not, and should not, limit the disclosed method to the particular disclosed order of steps.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description.

The invention claimed is:

1. A kit for incubating one or more O-rings with a sample fluid to allow binding to one or more biomarkers potentially present in the fluid, comprising:
   a) one or more O-rings, made of a polymer, each individually comprising an aperture; and
   b) a container configured to hold the one or more O-rings and the sample fluid such that the one or more O-rings can bind with the one or more biomarkers potentially present in the fluid via affinity chromatography.

2. The kit of claim 1, wherein the system comprises a plurality of O-rings that are of substantially the same size and shape, and are capable of binding to a plurality of biomarkers potentially present in the sample fluid.

3. The kit of claim 2, wherein the O-rings are coated with a coupling reagent to enhance binding to the plurality of biomarkers potentially present in the sample fluid.

4. The kit of claim 2, further comprising a plurality of capture molecules capable of covalently coupling with the plurality of O-rings, to form a plurality of O-ring/capture molecule complexes, wherein each capture molecule is selected to bind to a particular type of biomarker potentially present in the fluid.

5. The kit of claim 2, wherein the container is a deep well microplate, wherein a plurality of deep wells are configured to hold the plurality of O-rings.

6. The kit of claim 1, further comprising a probe having a central body with a cross-section that is smaller than the O-ring apertures such that it can traverse through multiple O-ring apertures to support said O-rings in a determined order.

7. The kit of claim 6, wherein the probe comprises a retainer at one end of the central body that has a larger cross-section than the O-ring apertures.

8. The kit of claim 7, wherein the probe comprises grooves positioned along the central body configured to individually hold a single O-ring.

9. A kit for incubating a plurality of O-rings with a sample fluid to allow binding to a plurality of biomarkers potentially present in the fluid, comprising:
   a) a plurality of O-rings, each individually comprising an aperture; and
   b) a container configured to hold the plurality of O-rings and the sample fluid such that the plurality of O-rings can individually bind with a plurality of biomarkers potentially present in the fluid via affinity chromatography, and wherein the plurality of O-rings are of substantially the same size and shape, and wherein the container is a pin plate having a plurality of pins configured to pass through the apertures of multiple O-rings.

10. The kit of claim 9, wherein multiple pins are configured to individually traverse through the apertures of multiple O-rings, such that said multiple O-rings are stacked in a trackable order on a given pin.

11. A kit for incubating a plurality of O-rings with a sample fluid to allow binding to a plurality of biomarkers potentially present in the fluid, comprising:
   a) a plurality of O-rings, each individually comprising an aperture; and
   b) a container configured to hold the plurality of O-rings and the sample fluid such that the plurality of O-rings can bind with the plurality of biomarkers potentially present in the fluid via affinity chromatography, and
   wherein the plurality of O-rings are of substantially the same size and shape, and the container is a deep well microplate, wherein a plurality of deep wells are configured to individually hold multiple O-rings, such that said multiple O-rings are stacked in a trackable order in a given well.

* * * * *